US010005814B2

(12) United States Patent
Rasmussen et al.

(10) Patent No.: US 10,005,814 B2
(45) Date of Patent: Jun. 26, 2018

(54) LIGAND FUNCTIONALIZED POLYMERS

(71) Applicant: 3M INNOVATIVE PROPERTIES COMPANY, St. Paul, MN (US)

(72) Inventors: Jerald K. Rasmussen, Woodville, WI (US); Kannan Seshadri, Woodbury, MN (US); Robert T. Fitzsimons, Jr., Minneapolis, MN (US); James I. Hembre, Plymouth, MN (US); Catherine A. Bothof, Stillwater, MN (US); Erin A. Satterwhite, Chatham, NJ (US); George W. Griesgraber, Eagan, MN (US); Yi He, Roseville, MN (US); Louis C. Haddad, Mendota Heights, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days. days.

(21) Appl. No.: 15/591,490

(22) Filed: May 10, 2017

(65) Prior Publication Data
US 2017/0240591 A1 Aug. 24, 2017

Related U.S. Application Data

(62) Division of application No. 13/848,336, filed on Mar. 21, 2013, now abandoned, which is a division of application No. 13/026,331, filed on Feb. 14, 2011, now Pat. No. 8,435,776.

(60) Provisional application No. 61/310,005, filed on Mar. 3, 2010.

(51) Int. Cl.
| | | |
|---|---|---|
| C08G 73/00 | (2006.01) |
| C07K 1/14 | (2006.01) |
| C12N 11/08 | (2006.01) |
| C08G 73/02 | (2006.01) |
| C08F 126/02 | (2006.01) |
| C08F 120/60 | (2006.01) |
| B01D 21/01 | (2006.01) |

(52) U.S. Cl.
CPC ............... *C07K 1/14* (2013.01); *B01D 21/01* (2013.01); *C08F 120/60* (2013.01); *C08F 126/02* (2013.01); *C08G 73/0206* (2013.01); *C12N 11/08* (2013.01)

(58) Field of Classification Search
None
See application file for complete search history.

(56) References Cited

U.S. PATENT DOCUMENTS

| | | |
|---|---|---|
| 24,906 A | 7/1859 | Goodfellow |
| 39,399 A | 8/1863 | Hull |
| 1,529,256 A | 3/1925 | Kelley |
| 2,945,006 A | 7/1960 | Minsk |
| 3,849,241 A | 11/1974 | Butin |
| 3,876,738 A | 4/1975 | Marinaccio |
| 3,928,517 A | 12/1975 | Knight |
| 4,031,038 A | 6/1977 | Grinstead |
| 4,062,886 A | 12/1977 | Turner |
| 4,118,531 A | 10/1978 | Hauser |
| 4,157,418 A | 6/1979 | Heilmann |
| 4,181,755 A | 1/1980 | Liu |
| 4,243,500 A | 1/1981 | Glennon |
| 4,266,044 A | 5/1981 | Timmerman |
| 4,303,485 A | 12/1981 | Levens |
| 4,304,705 A | 12/1981 | Heilmann |
| 4,339,473 A | 7/1982 | D'Agostino |
| 4,340,057 A | 7/1982 | Bloch |
| 4,346,142 A | 8/1982 | Lazear |
| 4,364,972 A | 12/1982 | Moon |
| 4,402,703 A | 9/1983 | Panto |
| T103,601 I4 | 11/1983 | Repetti |
| 4,473,474 A | 9/1984 | Ostreicher |
| 4,529,256 A | 7/1985 | Kretzschmar |
| 4,539,256 A | 9/1985 | Shipman |
| 4,563,388 A | 1/1986 | Bonk |
| 4,618,533 A | 10/1986 | Steuck |
| 4,619,979 A | 10/1986 | Kotnour |
| 4,707,265 A | 11/1987 | Barnes, Jr. |
| 4,726,989 A | 2/1988 | Mrozinski |
| 4,734,208 A | 3/1988 | Pall |
| 4,773,903 A | 9/1988 | Weisman |
| 4,777,276 A | 10/1988 | Rasmussen |
| 4,837,067 A | 6/1989 | Carey, Jr. |
| 4,843,134 A | 6/1989 | Kotnour |
| 4,845,132 A | 7/1989 | Masuoka |
| 4,867,881 A | 9/1989 | Kinzer |

(Continued)

FOREIGN PATENT DOCUMENTS

| | | |
|---|---|---|
| CA | 2422738 | 4/2002 |
| DE | 2630784 | 2/1977 |

(Continued)

OTHER PUBLICATIONS

Renard, Isabelle et al; "Identification and validation of the methylated twist1 and nid2 genes through real-time methylation-specific polymerase chain reaction assays for the inoninvasive detection fo primary bladder cancer in urine samples." Eur. Urol. (2010) 58 p. 96-104.*

"Functions Containing an Iminocarbonyl Group," Comprehensive Organic Functional Group Transformations II, vol. 6, Carbon with Three or Four Attached Hereroatoms, p. 639-643.

Amersham product literature on affinity chromatography (pamphlet 18-1022-29, edition AD, copyright 2002).

Barner, "Reversible Addition-Fragmentation Chain Transfer Graft Copolymerization of Styrene and m-Isopropenyl-α, α'-dimethylbenzyl Isocyanate from Polypropylene Lanterns: Solid Phases for Scavenging Applications." Journal of Polymer Science: Part A: Polymer Chemistry, vol. 44, pp. 857-864, (2006).

Barsbay, "Verification of Controlled Grafting of Styrene from Cellulose via Radiation-Induced RAFT Polymerization," Macromolecules, vol. 40, No. 20, pp. 7140-7147, (2007).

(Continued)

*Primary Examiner* — Fred H Reynolds
(74) *Attorney, Agent, or Firm* — Kent S. Kokko

(57) ABSTRACT

Ligand functionalized substrates, methods of making ligand functionalized substrates, and methods of using functionalized substrates are disclosed.

23 Claims, 4 Drawing Sheets

(56) References Cited

U.S. PATENT DOCUMENTS

| | | |
|---|---|---|
| 4,885,086 A | 12/1989 | Miura |
| 4,936,934 A | 6/1990 | Buehning |
| 4,944,879 A | 7/1990 | Steuck |
| 4,968,733 A | 11/1990 | Muller |
| 4,981,730 A | 1/1991 | Zaleski |
| 4,985,298 A | 1/1991 | Buckley |
| 5,006,247 A | 4/1991 | Dennison |
| 5,061,751 A | 10/1991 | Patton |
| 5,064,866 A | 11/1991 | Toyomoto |
| 5,071,880 A | 12/1991 | Takanobu |
| 5,075,342 A | 12/1991 | Ishigaki |
| 5,120,594 A | 6/1992 | Mrozinski |
| 5,160,627 A | 11/1992 | Cussler |
| 5,180,492 A | 1/1993 | Ohnishi |
| 5,200,471 A | 4/1993 | Coleman |
| 5,202,025 A | 4/1993 | Onishi |
| 5,208,111 A | 5/1993 | Decher |
| 5,209,849 A | 5/1993 | Hu |
| 5,229,172 A | 7/1993 | Cahalan |
| 5,260,360 A | 11/1993 | Mrozinski |
| 5,282,971 A | 2/1994 | Degen |
| 5,290,871 A | 3/1994 | Ahmed |
| 5,308,641 A | 5/1994 | Cahalan |
| 5,344,701 A | 6/1994 | Gagnon |
| 5,336,698 A | 8/1994 | Kashiwagi |
| 5,342,688 A | 8/1994 | Kitchin |
| 5,350,805 A | 9/1994 | Lin |
| 5,439,983 A | 8/1995 | Ahmed |
| 5,453,467 A | 9/1995 | Bamford |
| 5,458,782 A | 10/1995 | Hou |
| 5,503,746 A | 4/1996 | Gagnon |
| 5,506,279 A | 4/1996 | Babu |
| 5,531,900 A | 7/1996 | Raghavan |
| 5,532,112 A | 7/1996 | Kohler |
| 5,532,311 A | 7/1996 | Sirvio |
| 5,547,576 A | 8/1996 | Onishi |
| 5,578,400 A | 11/1996 | Gineste |
| 5,589,269 A | 12/1996 | Ali |
| 5,623,044 A | 4/1997 | Chiao |
| 5,627,217 A | 5/1997 | Rilling |
| 5,648,400 A | 7/1997 | Sugo |
| 5,652,050 A | 7/1997 | Pall |
| 5,712,027 A | 1/1998 | Ali |
| 5,736,051 A | 4/1998 | Degen |
| 5,741,543 A | 4/1998 | Winslow |
| 5,753,768 A | 5/1998 | Ellis |
| 5,766,478 A * | 6/1998 | Smith ................ B01D 61/16 210/638 |
| 5,773,485 A | 6/1998 | Bennett |
| 5,782,908 A | 7/1998 | Cahalan |
| 5,804,263 A | 9/1998 | Goldberg |
| 5,846,438 A | 12/1998 | Pall |
| 5,871,823 A | 2/1999 | Anders |
| 5,902,836 A | 5/1999 | Bennett |
| 5,906,734 A | 5/1999 | Girot |
| 5,914,182 A | 6/1999 | Drumheller |
| 5,962,544 A | 10/1999 | Waller, Jr. |
| 6,033,719 A | 3/2000 | Keogh |
| 6,039,872 A | 3/2000 | Wu |
| 6,040,315 A | 3/2000 | Day |
| 6,056,529 A | 5/2000 | Meyering |
| 6,063,484 A | 5/2000 | Exsted |
| 6,096,293 A | 8/2000 | Stringer |
| 6,096,369 A | 8/2000 | Anders |
| 6,197,289 B1 | 3/2001 | Wirt |
| 6,230,776 B1 | 5/2001 | Choi |
| 6,245,922 B1 | 6/2001 | Heilmann |
| 6,258,276 B1 | 7/2001 | Mika |
| 6,264,044 B1 | 7/2001 | Meyering |
| 6,267,916 B1 | 7/2001 | Meyering |
| 6,280,853 B1 | 8/2001 | Mickols |
| 6,287,730 B1 | 9/2001 | Callahan |
| 6,294,163 B1 | 9/2001 | Dhal |
| 6,294,249 B1 | 9/2001 | Hamer |
| 6,315,130 B1 | 11/2001 | Olsen |
| 6,387,379 B1 | 5/2002 | Goldberg |
| 6,391,200 B2 | 5/2002 | Pulek |
| 6,413,070 B1 | 7/2002 | Meyering |
| 6,448,301 B1 | 9/2002 | Babu |
| 6,458,269 B1 | 10/2002 | Bassett |
| 6,464,084 B2 | 10/2002 | Pulek |
| 6,506,847 B1 | 1/2003 | Song |
| 6,513,666 B2 | 2/2003 | Meyering |
| 6,521,011 B1 | 2/2003 | Sundet |
| 6,537,411 B1 | 3/2003 | Kang |
| 6,596,167 B2 | 7/2003 | Ji |
| 6,617,142 B2 | 9/2003 | Keogh |
| 6,635,104 B2 | 10/2003 | Komkova |
| 6,660,376 B1 | 12/2003 | Zimmel |
| 6,669,994 B2 | 12/2003 | Swan |
| 6,712,966 B1 | 3/2004 | Pulek |
| 6,734,256 B1 | 5/2004 | Everaerts |
| 6,743,878 B2 | 6/2004 | Bowers |
| 6,773,654 B2 | 8/2004 | Sugo |
| 6,776,940 B2 | 8/2004 | Meyering |
| 6,811,837 B2 | 11/2004 | Iwasa |
| 6,818,038 B2 | 11/2004 | Sugo |
| 6,828,386 B2 | 12/2004 | MacKinnon |
| 6,844,371 B1 | 1/2005 | Komatsu |
| 6,852,802 B1 | 2/2005 | Komatsu |
| 6,861,001 B2 | 3/2005 | Lee |
| 6,939,466 B2 | 9/2005 | Pulek |
| 7,048,855 B2 | 5/2006 | de la Cruz |
| 7,067,058 B2 | 6/2006 | Yeh |
| 7,073,671 B2 | 7/2006 | Charkoudian |
| 7,094,469 B2 | 8/2006 | Moya |
| 7,101,621 B2 | 9/2006 | Smith |
| 7,112,389 B1 | 9/2006 | Arora |
| 7,125,603 B2 | 10/2006 | David |
| 7,135,230 B2 | 11/2006 | Nakao |
| 7,158,400 B2 | 1/2007 | Fang |
| 7,160,464 B2 | 1/2007 | Lee |
| 7,169,933 B2 | 1/2007 | Benson |
| 7,170,739 B1 | 1/2007 | Arora |
| 7,178,676 B2 | 2/2007 | Pulek |
| 7,204,997 B2 | 4/2007 | Bromberg |
| 7,235,122 B2 | 6/2007 | Bryner |
| 7,247,370 B2 | 7/2007 | Childs |
| 7,276,247 B2 | 10/2007 | Fansler |
| 7,284,668 B2 | 10/2007 | Chakoudian |
| 7,294,743 B2 | 11/2007 | Algotsson |
| 7,300,984 B2 | 11/2007 | MacKinnon |
| 7,316,919 B2 | 1/2008 | Childs |
| 7,338,692 B2 | 3/2008 | Smith |
| 7,361,767 B2 | 4/2008 | Benson |
| 7,374,416 B2 | 5/2008 | Cook |
| 7,402,678 B2 | 7/2008 | Benson |
| 7,459,085 B2 | 12/2008 | Koguma |
| 7,459,489 B2 | 12/2008 | Lewandowski |
| 7,553,417 B2 | 6/2009 | Waller, Jr. |
| 7,604,746 B2 | 10/2009 | Childs |
| 7,612,122 B2 | 11/2009 | Herlihy |
| 7,628,917 B2 | 12/2009 | Penezina |
| 7,645,312 B2 | 1/2010 | Hamlin |
| 7,652,103 B2 | 1/2010 | Kavanagh |
| 7,658,994 B2 | 2/2010 | Lakshmi |
| 7,691,915 B2 | 4/2010 | Kim |
| 7,714,076 B2 | 5/2010 | Krepski |
| 7,727,434 B2 | 6/2010 | Kniajanski |
| 7,807,754 B2 | 10/2010 | Sherman |
| 7,838,110 B2 | 11/2010 | Zhu |
| 7,870,794 B2 | 1/2011 | Bickmann |
| 7,883,767 B2 | 2/2011 | Childs |
| 8,377,672 B2 | 2/2013 | Rasmussen |
| 8,435,776 B2 | 5/2013 | Rasmussen |
| 8,551,894 B2 | 10/2013 | Seshadri |
| 8,652,582 B2 | 2/2014 | Bothof |
| 2002/0028910 A1 | 3/2002 | Fry |
| 2004/0016028 A1 | 6/2004 | Bryner |
| 2004/0116026 A1 | 6/2004 | Kubose |
| 2005/0025911 A1 | 2/2005 | Kasperchik |
| 2005/0040109 A1 | 2/2005 | Smith |
| 2005/0095266 A1 | 5/2005 | Perichaud |
| 2005/0118425 A1 | 6/2005 | Childs |

(56) References Cited

U.S. PATENT DOCUMENTS

| | | |
|---|---|---|
| 2005/0199335 A1 | 9/2005 | Oehl |
| 2005/0266582 A1 | 12/2005 | Modlin |
| 2006/0178070 A1 | 8/2006 | Kritzer |
| 2007/0042015 A1 | 2/2007 | Berry |
| 2007/0065490 A1 | 3/2007 | Schabert |
| 2007/0154651 A1 | 7/2007 | Weiss |
| 2007/0221569 A1 | 9/2007 | Stouffer |
| 2007/0299211 A1 | 12/2007 | Chen |
| 2008/0017578 A1 | 1/2008 | Childs |
| 2008/0107690 A1 | 5/2008 | Dake |
| 2008/0193981 A1 | 8/2008 | Fahrner |
| 2008/0230471 A1 | 9/2008 | Tamada |
| 2008/0264867 A1 | 10/2008 | Mika |
| 2009/0020472 A1 | 1/2009 | Lucas |
| 2009/0032463 A1 | 2/2009 | Childs |
| 2009/0035552 A1 | 2/2009 | Childs |
| 2009/0098359 A1 | 4/2009 | Waller, Jr. |
| 2009/0176052 A1 | 7/2009 | Childs |
| 2010/0075131 A1 | 3/2010 | Seshadri |
| 2010/0075560 A1 | 3/2010 | Seshadri |
| 2010/0111881 A1 | 5/2010 | Huang |
| 2010/0155323 A1 | 6/2010 | Weiss |
| 2010/0320138 A1 | 12/2010 | Waller |
| 2010/0331484 A1 | 12/2010 | Swift |
| 2011/0033633 A1 | 2/2011 | Bothof |
| 2012/0045400 A1 | 2/2012 | Nowak |
| 2012/0252091 A1 | 10/2012 | Rasmussen |
| 2013/0137158 A1 | 5/2013 | Rasmussen |
| 2014/0004595 A1 | 1/2014 | Seshadri |
| 2014/0087445 A1 | 3/2014 | Bothof |

FOREIGN PATENT DOCUMENTS

| | | |
|---|---|---|
| EP | 0472990 | 3/1992 |
| EP | 0 632 329 | 1/1995 |
| EP | 0 779 387 | 6/1997 |
| EP | 0 860 213 | 8/1998 |
| EP | 1 228 756 | 8/2002 |
| EP | 1 552 878 | 7/2005 |
| EP | 2027921 | 2/2009 |
| EP | 2 036 930 | 3/2009 |
| JP | 62298405 | 12/1987 |
| JP | 63240902 | 10/1988 |
| JP | 5111607 | 5/1993 |
| JP | 08290066 | 11/1996 |
| JP | 10085572 | 4/1998 |
| JP | 10279713 | 10/1998 |
| JP | 2002371471 | 12/2002 |
| JP | 2003301059 | 10/2003 |
| JP | 2004073943 | 3/2004 |
| JP | 2007-049966 | 3/2007 |
| WO | WO 1989/09246 | 10/1989 |
| WO | WO 1995/10552 | 4/1995 |
| WO | WO 1997/05100 | 2/1997 |
| WO | WO 1997/18904 | 5/1997 |
| WO | WO 2000/01468 | 1/2000 |
| WO | WO 2000/22032 | 4/2000 |
| WO | WO 2000/050161 | 8/2000 |
| WO | WO 2000/54866 | 9/2000 |
| WO | WO 2001/96487 | 12/2001 |
| WO | WO 2002/060509 | 8/2002 |
| WO | WO 2003/008011 | 1/2003 |
| WO | WO 2003/055923 | 7/2003 |
| WO | WO 2004/02714 | 1/2004 |
| WO | WO 2004/004679 | 1/2004 |
| WO | WO 2005/035641 | 4/2005 |
| WO | WO 2005/040092 | 5/2005 |
| WO | WO 2005/092403 | 10/2005 |
| WO | WO 2007/001405 | 1/2007 |
| WO | WO 2007/078878 | 7/2007 |
| WO | WO 2007/078880 | 7/2007 |
| WO | WO 2008/008872 | 1/2008 |
| WO | WO 2008/100713 | 8/2008 |
| WO | WO 2008/100755 | 8/2008 |
| WO | WO 2009/085726 | 7/2009 |
| WO | WO 2009/086347 | 7/2009 |
| WO | WO 2009/102623 | 8/2009 |
| WO | WO 2009/120420 | 10/2009 |
| WO | WO 2009/127285 | 10/2009 |
| WO | WO 2009/146321 | 12/2009 |
| WO | WO 2009/148869 | 12/2009 |
| WO | WO 2010/033794 | 3/2010 |
| WO | WO 2010/033807 | 3/2010 |

OTHER PUBLICATIONS

Bennhold, Hermann and Kallee, Ekkehard; "Comparative studies on the half life of i131 labeled albumins and nonradioactive human serum albumin in a case of analbuminemia." J. Clin. Invest. (1959) 38(5) p. 863-872.

Bolto , "Organic polyelectolytes in water treatment," Water Research, vol. 41, pp. 2301-2324. (2007).

Buehler , "Solvent Effects on the Permeability of Membrane-Supported Gels," Ind. Eng. Chem. Res., vol. 41, No. 3, pp. 464-472, (2002).

Burke, J., "Solubility Parameters: Theory and Application," AIC Book and Paper Group Annual, vol. 3, pp. 13-58, (1984).

Bustamante, Heriberto A. et al; "Interaction between cryptosporidium oocysts and water treatment coagulants." Wat. Res. (2001) 35(13) p. 3179-3189.

"Grafting copolymerization of acrylamides onto preirradiated PP Films," Radiation Physics and Chemistry, vol. 55, pp. 87-92, (1999).

Childs, "Nanofiltration using pore-filled membranes: effect of polyelectrolyte composition on performance", Separation and Purification Technology; vol. 22-23, pp. 507-517, (2001).

Davies, "The Separation of Airborne Dust and Particles," The Institution of Mechanical Engineers, Proceedings (B), vol. 1B, Nos. 1-12, pp. 185-213, (1952-1953).

Decher, "Buildup of ultrathin multilayer films by a self-assembly process: III. Consecutively alternating adsorption of anionic and cationic polyelectrolytes on charged surfaces," Thin Solid Films, vol. 210/211, pp. 831-835, (1992).

Definition of stoma from biology-online.org (www.biology-online.org/dictionary/Stoma, downloaded Mar. 29, 2014).

DuPont™ brochure entitled, "DuPont™ Hybrid Membrane Technology—Nanofiber Science to Revolutionize Filtration, Energy Storage and Beyond," Copyright © 2007, 4 pages.

Epomin, a polyethylenimine (https://www.shokubai.co.jp/en/products/functionally/epomin1.html) downloaded Apr. 1, 2014.

Exendin (protein data bank accession No. AAB51130, downloaded Apr. 3, 2014.

Fisher Scientific 2005-05 catalog, p. 497.

Fraenkel-Conrat, Heinz and Olcott, Harold S.; "The reaction of formaldehyde with proteins. V. Crosslinking between amino and primary amide or guanidyl group." J. Am. Chem. Soc. (1948) 70, p. 2673-2684.

Franken, "Wetting Criteria for the Applicability of Membrane Distillation," Journal of Membrane Science, vol. 33, pp. 315-328, (1987).

Ghosh, "Protein separation using membrane chromatography: opportunities and challenges," Journal of Chromatography A., vol. 952, Issues 1-2, pp. 13-27, Apr. 5, 2002.

Grasselli, "Electron-beam induced RAFT-graft polymerization of poly(acrylic acid) onto PVDF," Nuclear Instruments and Methods in Physics Research B, vol. 236, pp. 202-207, (2005).

Gupta, Preirradiation grafting of acrylonitrile onto polypropylene monofilament for biomedical applications: I. Influence of synthesis conditions, Radiation Physics and Chemistry, vol. 75, pp. 161-167, (2006).

Holladay, April; "Lightening strikes fish, predators eat rotten meat, everst scrapes stratosphere." USA Today, posted online Mar. 5, 2004, http://usatoday30.usatoday.com/tech/columnist/aprilholloday/2004-03-05-wonderquest_xthm.

Huang, "Immobilization of *Eschericia coli* Cells Using Porous Support Particles Coated with Cationic Polymers," Journal of Bioscience and Bioengineering, vol. 104, No. 2, pp. 98-103, (2007).

(56) References Cited

OTHER PUBLICATIONS

Hubner, "Makromolekulare Chem," vol. 11, Nos. 109-124, pp. 109-124, (1970).
"pH-Sensitive Gating by Conformational Change of a Polypeptide Brush Grafted onto a Porous Polymer Membrane," Journal of the American Chemical Society, vol. 119, pp. 1619-1623, (1997).
Iwakura, "A Novel Preparation of Pseudoxzaolones," Tetraheron, vol. 23, pp. 3363-3373, Pergamon Press Ltd, (1967).
Jianqin, "Pre-irradiation grafting of temperature sensitive hydrogel on cotton cellulose fabric," Radiation Physics and Chemistry, vol. 55, pp. 55-59, (1999).
Jonas, Wayne et al, "Metals and health: a clinical toxiclogical perspective on tungsten and review of the literature." Mil. Med. (2007) 172(9) p. 1002-1006.
Kanani, "Separation of human plasma proteins HAS and HIgG using high-capacity macroporous gel-filled membranes," Biochemical Engineering Journal, vol. 35, pp. 295-300, (2007).
Kanani, "Protein bioseparation by membrane chromatography using polyelectrolyte gel-coated adsorptive membranes," Department of Chemical Engineering, McMaster University, 7 pages.
Kavakli, "Radiation-induced grafting of dimethylaminoethylmethacrylate onto PE/PP nonwoven fabric," Science Direct, Nuclear Instruments and Methods in Physics Research B, vol. 265, pp. 204-207, (2007).
Kawai, "Protein binding to polymer brush, based on ion-exchange, hydrophobic, and affinity interactions," Journal of Chromatography B, vol. 790, Issues 1-2, pp. 131-142, Jun. 25, 2003.
Kiani, K. "Raft Mediated Surface Grafting of t-Butyl Acrylate onto an Ethylene-Propylene Copolymer Initiated by Gamma-Radiation," Journal of Polymer Science: Part A: Polymer Chemistry, vol. 45, 2007, pp. 1074-1083.
Kim, "Diffusion and Flow through Polymer-Lined Micropores," Ind. Eng. Chem. Res., vol. 30, pp. 1008-1016, (1991).
Kolarz, "New selective resin with guanidyl groups," Reactive & Functional Polymers, vol. 36, pp. 185-195, 1998.
Kulkarni, "Effect of Asymmetric Centers on Free Radical Polymerization and the Properties of Polymers: Methacrylyl Alanine, methacrylyl Glutamic Acid, Acrylyl Glutamic Acid, and Their Polymers," Journal of Polymer Science, vol. 54, pp. 491-503, (1961).
Latulippe, "Characterization of Gel-Filled Membranes for Plasma Protein Fractionation," Department of Chemical Engineering, McMaster University, 4 pages.
Leofanti, G.; "Surface area and pore texture of catalysts." Catalysis Today (1998) 41 p. 207-219.
Lingwood, Clifford A.; "Production of glycolipid affinity matrices by use of heterobifunctional crosslinking agents." J. Lipid. Res. (1984) 25 p. 1010-1012.
Litt, Michael D. et al; "Correlation between histone lysine methylation and developmental changes at the chicken beta-globin locus." Science (2001) 293 p. 2453-2455.
Majors, Ronald E.; "New chromatography columns and accessories at the 2005 pittcon conference: part II." LC-GC North America (2005) 23(4).
Margni, R.A. et al; "Agglutinating and non-agglutinating antibodies in rabbits inoculated with a particulate antigen (*Salmonella typhimurium*)" Immunol. (1983) 48, p. 351-359.
Middleton, Jim et al; "Leukocyte extravasation: chemokine transport and presentation by the endothelium." Blood (2002) 100 p. 3853-3860.
Mika, "Acid/base properties of poly(4-vinylpyridine) anchored within microporous membranes," Journal of Membrane Science, vol. 152, pp. 129-140, (1999).
Mika, "Chemical valves based on poly(4-vinylpyridine)-filled microporous membranes," Journal of Membrane Science, vol. 153, pp. 45-56, (1999).
Mika, "Porous, polyelectrolyte-filled membranes: Effect of crosslinking on flux and separation", Journal of Membrane Science, vol. 135, pp. 81-92, (1997).
Mika, "Salt separation and hydrodynamic permeability of porous membrane filled with pH-sensitive gel," Journal of Membrane Science, vol. 206, pp. 19-30, (2002).
"A new class of polyelectrolyte-filled microfiltration membranes with environmentally controlled porosity", Journal of Membrane Science, vol. 108, pp. 37-56, (1995).
"Poly(4-vinylpyridine)-filled microfiltration membranes: physicochemical properties and morphology", Journal of Membrane Science, vol. 136, pp. 221-232, (1997).
Millipore technical brief on leachables and extractables (https://www.millipore.com/publications.nsf/a73664f9f981af8c852569b9005b4ee/42462e2f03f45ac4825783400728c76/$FILE/PB10010000.pdf downloaded Mar. 29, 2014.
Munthe-Kaas, M.C. et al; "Eosinophil cationic protein (ecp) polymorphisims and association with asthma, s-ecp levels and related phenotypes." Allergy (2007) 62 p. 429-436.
"Grafting polymerization of styrene onto preirradiated polypropylene fabric," Radiation Physics and Chemistry, vol. 54, pp. 317-322, (1999).
Osada, "Control of Water Permeability by Mechanochemical Contraction of Poly(Methacrylic Acid)-Grafted Membranes," Journal of Membrane Science, vol. 27, pp. 327-338, (1986).
Oudin, Jacques; "Allotypy of rabbit serum proteins." J.. Exp. Med. (1960) 112(1) p. 107-24.
Padovani, Bernard et al; "Pulmonary embolism caused by acrylic cement: a rare complication of percutaneous vertebroplasty." AJNR Am. J. Neuroradiol (1992) 20 p. 375-377.
Pietrucha, "Effect of Chain Transfer Agent on the Radiation Grafting of Methyl Methacrylate Onto Chromium (III) Crosslinked Collagen," Journal of Radioanalytical and Nuclear Chemistry, vol. 149, No. 2, pp. 327-331, (1991).
Protein data base entry form integrin (accession No. NP_004754), downloaded Apr. 2, 2014.
Reed, Roberta B. et al; "Non-resoluving jaundice: billrubin covalently attached to serum albumin circulates with the same metabolic half life as albumin." Clin. Chem. (1988) 34(10) p. 1992-1994.
Reynolds et al, Anal. Chem. (2005) 77(3) p. 814-817.
Richard R. Burgess, Protein Precipitation Techniques, 2009, Methods in Enzymology, Chapter 20, 331-342.
Riske, "The use of chitosan as a flocculant in mammalian cell culture dramatically improves clarification throughput without adversely impacting monoclonal antibody recover," Journal of Biotechnology, vol. 128, pp. 813-823, (2007).
"Bisdiguanides having Antibacterial Activity," Chem Soc., pp. 4422-4425 (1956).
Ruoslahti, Erkki and Engvall, Eva; "Perspectives series: cell adhesion in vascular biology." J. Clin. Invest. (1997) 99(6) p. 1149-1152.
Sahu, Kalyanasis et al; Study of interaction of a cationic protein with a cationic surfactant using solvation dynamics lysozyme: ctab, Chem. Phys. Lett. (2005) p. 484-489.
Sequence of one chain of fibrin, protein data bank, accession No. 1fzf_f, downloaded Mar. 29, 2014.
Shah, Nalini et al; "Effect of guar gum, lignin, and pectin on proteolytic enzyme levels in the gastrointestinal tract of the rat: a time based study." J. Nutr. (1986) 116, p. 786-794.
Shaozao, "Effect of Gamma Ray Irradiation on Properties of Polypropylene Fibers and Nonwoven Fabrics," vol. 22, No. 6, pp. 18-21, (1999).
Shiratori, "pH-Dependent Thickness Behavior of Sequentially Adsorbed Layers of Weak Polyelectrolytes," Macromolecules, vol. 33, pp. 4213-4219, (2000).
Simoncic, Paul Daniel; "Application of hetero diels-alder methodology towards the synthesis of martinelline." Thesis, Jan. 1999, University of Toronto.
Stryer, Lubert Biochemistry, ISBN 0-7167-1843-X, 1988.
Suryanarayan, "The effect of gel layer thickness on the salt rejection performance of polyelectrolyte gel-filled nanofiltration membranes," Journal of Membrane Science, vol. 290, pp. 196-206, (2007).
Tashiro, "Removal of Eschericia coli from Water by Systems Based on Insoluble Polystyrene-Poly(ethylene Glycol)s, -Poly-

(56) References Cited

OTHER PUBLICATIONS ethylenimines, and -Polyethylenepolyamines Quaternized," Journal of Applied Polymer Science, vol. 43, pp. 1369-1377, (1991).
Taylor, "The Synthesis of Vinyl Peptide Monomers," Journal of Polymer Science, Polymer Letters, vol. 7, p. 597-603, (1969).
The entry for human albumin in the protein data bank (accession No. AAA98797), downloaded Apr. 3, 2014.
The NIH medline plus entry for the stomach acid test (http://www.nlm.nih.gov/medlineplus/ency/article/003883.htm, downloaded Jun. 9, 2014).
The protein data bank entry accession No. 1NQB_C., downloaded Apr. 3, 2014.
The recipe for PEI reagent, Cold Spring harb. Protoc. (2006).
U.S. Appl. No. 12/986,485 entitled "Ligand Functionalized Polymers," filed Jan. 7, 2011.
Ulbricht, "Porous Polypropylene Membranes with Different Carboxyl Polymer Brush Layers for Reversible Protein Binding via Surface-Initiated Graft Copolymerization," Chem. Mater, vol. 17, No. 10, pp. 2622-2631, (2005).
Ulbricht, "Advanced functional polymer membranes," Polymer, vol. 47, pp. 2217-2262, (2007).
Webpage for Epomine polyethyleneimine (https://www.shokubai.co.jp/en/products/functionality/epomin.1.html, downloaded Mar. 29, 2014.

Wente, Manufacture of Superfine Organic Fibers, (Navel Research Laboratories Report No. 4364, 1954).
Wente, Superfine Thermoplastic Fibers, 48 Indus. Eng. Chem. 1342 (1956).
Winnik, "Polyacrylic acid pore-filled microporous membranes and their use in membrane-mediated synthesis of nanocrystalline ferrihydrite," Can. J. Chem., vol. 76, pp. 10-17, (1998).
Worthington biochemical's catalog entry for pepsin (http://www.worthington-biochem.com/pm/default.html, downloaded Jun. 9, 2014).
Zawadzki, H.J.; "New coordination compounds of copper(ii) with guanidinopyrimidines in n, n-dimethylformamide." Polish J. Chem. (2000) 74, p. 935-944.
Zazzera, "XPS and SIMS Study of Anhydrous HF and UV/Ozone-Modified Silicon (100) Surfaces," J. Electrochem. Soc., vol. 136, No. 2, pp. 484-491, (1989).
Zhang, "pH Control of Transport through a Porous Membrane Self-Assembled with a Poly(acrylic acid) Loop Brush," Langmuir, vol. 17, pp. 8336-8340, (2001).
Zhou, "Pore-filled nanofiltration membranes based on poly(2-acrylamido-2-methylpropanesulfonic acid) gels," Journal of Membrane Science, vol. 254, pp. 89-99, (2005).

\* cited by examiner

LIGAND FUNCTIONALIZED POLYMERS

CROSS REFERENCE TO RELATED APPLICATIONS

This application is a divisional of U.S. application Ser. No. 13/848,336, filed Mar. 21, 2013, which is a divisional of U.S. application Ser. No. 13/026,331, filed Feb. 14, 2011, now issued as U.S. Pat. No. 8,435,776, issued May 7, 2013, which claims the benefit of U.S. Application No. 61/310,005, filed Mar. 3, 2010, the disclosure of which is incorporated by reference in its/their entirety herein.

TECHNICAL FIELD

The present disclosure relates to ligand-functionalized polymers, and methods for preparing the same. The functionalized polymers are useful in selectively binding and removing biological materials, such as viruses, from biological samples.

BACKGROUND

Detection, quantification, isolation and purification of target biomaterials, such as viruses and biomacromolecules (including constituents or products of living cells, for example, proteins, carbohydrates, lipids, and nucleic acids) have long been objectives of investigators. Detection and quantification are important diagnostically, for example, as indicators of various physiological conditions such as diseases. Isolation and purification of biomacromolecules are important for therapeutic uses and in biomedical research. Biomacromolecules such as enzymes which are a special class of proteins capable of catalyzing chemical reactions are also useful industrially; enzymes have been isolated, purified, and then utilized for the production of sweeteners, antibiotics, and a variety of organic compounds such as ethanol, acetic acid, lysine, aspartic acid, and biologically useful products such as antibodies and steroids.

In their native state in vivo, structures and corresponding biological activities of these biomacromolecules are maintained generally within fairly narrow ranges of pH and ionic strength. Consequently, any separation and purification operation must take such factors into account in order for the resultant, processed biomacromolecule to have potency.

The use of certain ionic polymers, especially cationic polymers, for the flocculation of cell and/or cell debris, as well as for the precipitation of proteins, is known. Similarly, ionic polymers have been used to modify filtration media to enhance the removal of impurities from process streams in depth filtration or membrane absorber type applications. The effectiveness of these flocculants is typically reduced as the conductivity of the media being processed increases, i.e. as the salt content increases. There is a need in the art for polymeric materials with increased affinity for biological species under high ionic strength conditions.

Chromatographic separation and purification operations can be performed on biological product mixtures, based on the interchange of a solute between a moving phase, which can be a gas or liquid, and a stationary phase. Separation of various solutes of the solution mixture is accomplished because of varying binding interactions of each solute with the stationary phase; stronger binding interactions generally result in longer retention times when subjected to the dissociation or displacement effects of a mobile phase compared to solutes which interact less strongly and, in this fashion, separation and purification can be effected.

Most current capture or purification chromatography is done via conventional column techniques. These techniques have severe bottlenecking issues in downstream purification, as the throughput using this technology is low. Attempts to alleviate these issues include increasing the diameter of the chromatography column, but this in turn creates challenges due to difficulties of packing the columns effectively and reproducibly. Larger column diameters also increase the occurrence of problematic channeling. Also, in a conventional chromatographic column, the absorption operation is shut down when a breakthrough of the desired product above a specific level is detected. This causes the dynamic or effective capacity of the adsorption media to be significantly less than the overall or static capacity. This reduction in effectiveness has severe economic consequences, given the high cost of some chromatographic resins.

Polymeric resins are widely used for the separation and purification of various target compounds. For example, polymeric resins can be used to purify or separate a target compound based on the presence of an ionic group, based on the size of the target compound, based on a hydrophobic interaction, based on an affinity interaction, or based on the formation of a covalent bond. There is a need in the art for polymeric substrates having enhanced affinity for viruses and other biological species to allow selective removal from a biological sample. There is further need in the art for ligand functionalized membranes that overcome limitations in diffusion and binding, and that may be operated at high throughput and at lower pressure drops.

SUMMARY OF THE INVENTION

The present invention is directed to ligand-functionalized polymers, and methods of making the same. More specifically, the ligand-functionalized polymer includes a polyamine polymer, which has been modified to provide grafted ligand groups having the requisite affinity for binding neutral or negatively charged biomaterials, such as cells, cell debris, bacteria, spores, viruses, nucleic acids, and proteins.

In some embodiments, the ligand-functionalized polymer may be used as a flocculant whereby a biological sample, such as a cell culture fluid, is contacted causing negative and/or neutral species to bind to the polymer and precipitate from the solution or suspension. In another embodiment, a base substrate, such as a microporous membrane, may be coated with the ligand-functionalized polymer.

Methods of making a ligand functionalized substrate are provided. In some embodiments, the method comprises reacting a polyamine polymer with a guanylating agent, optionally in the presence of an acid catalyst.

A functionalized polymer is provided, having grafted pendent ligand groups, of the formula:

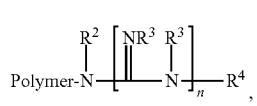

wherein
$R^2$ is a H, $C_1$-$C_{12}$ alkyl, $C_5$-$C_{12}$ (hetero)aryl, or a residue of the polymer chain;
each $R^3$ is independently H, $C_1$-$C_{12}$ alkyl, or $C_5$-$C_{12}$ (hetero)aryl, each $R^4$ is H, $C_1$-$C_{12}$ alkyl or alkylene, $C_5$-$C_{12}$ (hetero)aryl or (hetero)arylene, cyano, or —C(=NH)—N($R^2$)-Polymer, and n is 1 or 2.

It will be recognized that the "Polymer-N($R^2$)—" group of Formula I is the linkage formed between an amine group of polyamino polymer and the guanylating agent.

As used herein, "alkyl" or "alkylene" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent.

As used herein, "aryl" or "arylene" is an aromatic group containing 5-12 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

DETAILED DESCRIPTION OF THE INVENTION

Figure 1:
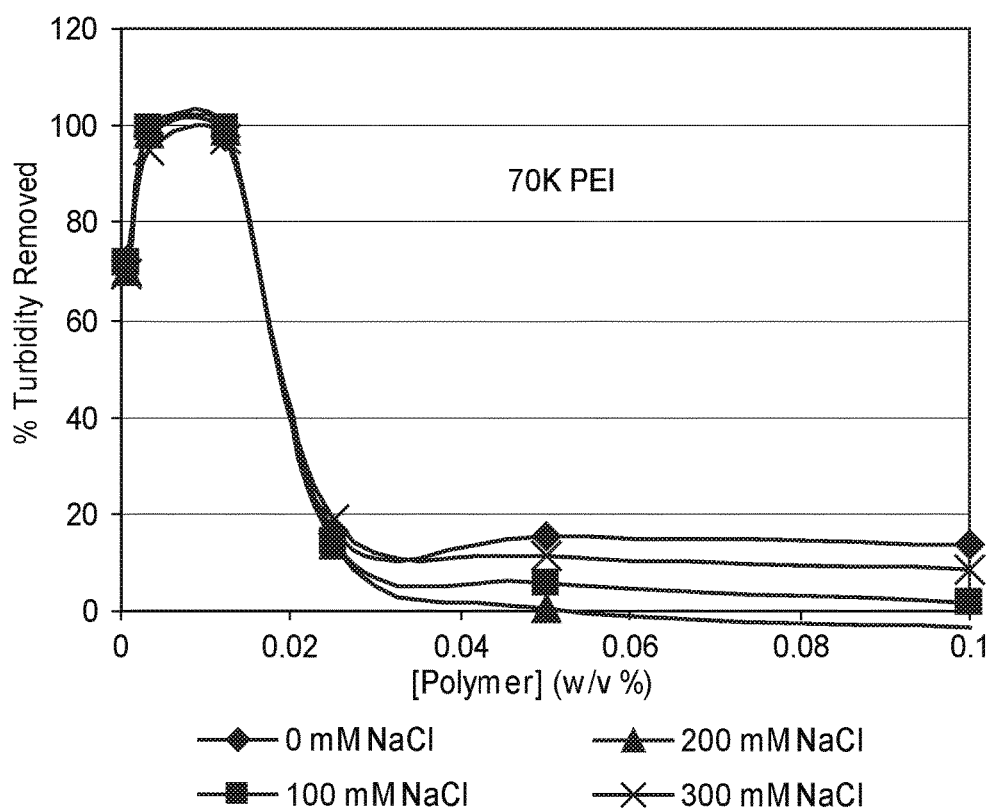
FIGS. 1 to 4 are plots of the *Geobacillus stearothermophilus* flocculation data of Example 35.

In the article and methods of this invention, ligand-functionalized polymers are provided which have enhanced affinity, especially in high ionic strength media, for neutral or negatively charged biological materials such as host cell proteins, DNA, RNA, viruses, and other microorganisms. The affinity for such biomaterials allows positively charged materials, such as antibodies, to be purified, as they are not bound to the ligand functional groups. The ligand functionalized substrate allows the selective capture or binding of target biomaterials by the ligand groups, while other materials, lacking the affinity for the ligand groups are passed. In some embodiments the ligand functionalized polymer is used as a flocculant to selectively bind target biomaterials, precipitate them from solution, and the precipitated adduct subsequently separated.

Polyamine Polymer

The base polymer comprises a polyamine polymer; i.e. a polymer having primary or secondary amino groups that may be pendent or catenary, i.e. in the polymer chain. The aminopolymers contain primary or secondary amine groups and can be prepared by chain growth or step growth polymerization procedures with the corresponding monomers. These monomers can also, if desired, be copolymerized with other monomers. The polymer can also be a synthesized or naturally occurring biopolymer. If any of these polymers, irrespective of source, do not contain primary or secondary amine groups, these functional groups can be added by the appropriate graft chemistry.

Useful aminopolymers are water soluble or water-dispersible. As used herein, the term "water soluble" refers to a material that can be dissolved in water. The solubility is typically at least about 0.1 gram per milliliter of water. As used herein, the term "water dispersible" refers to a material that is not water soluble but that can be emulsified or suspended in water.

Examples of amino polymers suitable for use, which are prepared by chain growth polymerization include, but are not limited to: polyvinylamine, poly(N-methylvinylamine), polyallylamine, polyallylmethylamine, polydiallylamine, poly(4-aminomethyl styrene), poly(4-aminostyrene), poly(acrylamide-co-methylaminopropylacrylamide), and poly(acrylamide-co-aminoethylmethacrylate).

Examples of amino polymers suitable for use, which are prepared by step growth polymerization include, but are not limited to: polyethylenimine, polypropylenimine, polylysine, polyaminoamides, polydimethylamine-epichlorohydrin-ethylenediamine, and any of a number of polyaminosiloxanes, which can be built from monomers such as aminopropyltriethoxysilane, N-(2-aminoethyl)-3-aminopropyltrimethoxysilane, N-trimethoxysilylpropyl-N-methylamine, and bis(trimethoxysilylpropyl)amine.

Useful aminopolymers that have primary or secondary amino end groups include, but are not limited to, those formed from polyamidoamine (PAMAM) and polypropylenimine: e.g. DAB-Am and PAMAM dendrimers (or hyperbranched polymers containing the amine or quaternary nitrogen functional group). Exemplary dendrimeric materials formed from PAMAM are commercially available under the trade designation Starburst™ (PAMAM) dendrimer" (e.g., Generation 0 with 4 primary amino groups, Generation 1 with 8 primary amino groups, Generation 2 with 16 primary amino groups, Generation 3 with 32 primary amino groups, and Generation 4 with 64 primary amino groups) from Aldrich Chemical, Milwaukee, Wis. Dendrimeric materials formed from polypropylenimine is commercially available under the trade designation "DAB-AM" from Aldrich Chemical. For example, DAB-Am-4 is a generation 1 polypropylenimine tetraamine dendrimer with 4 primary amino groups, DAB-Am-8 is a generation 2 polypropylenimine octaamine dendrimer with 8 primary amino groups, DAB-Am-16 is a generation 3 polypropylenimine hexadecaamine with 16 primary amino groups, DAB-Am-32 is a generation 4 polypropylenimine dotriacontaamine dendrimer with 32 primary amino groups, and DAB-Am-64 is a generation 5 polypropylenimine tetrahexacontaamine dendrimer with 64 primary amino groups.

Examples of aminopolymers suitable for use, which are biopolymers include chitosan, and starch, where the latter is grafted with reagents such as methylaminoethylchloride.

Other categories of aminopolymers suitable for use include polyacrylamide homo- or copolymers with amino monomers including aminoalkyl(meth)acrylate, (meth)acrylamidoalkylamine, and diallylamine.

Preferred aminopolymers include polyaminoamides, polyethyleneimine, polyvinylamine, polyallylamine, and polydiallylamine.

Suitable commercially available aminopolymers include, but are not limited to, polyamidoamines such as ANQUAMINE™ 360, 401, 419, 456, and 701 (Air Products and Chemicals, Allentown, Pa.); LUPASOL™ polyethylenimine polymers such as FG, PR 8515, Waterfree, P, PS (BASF Corporation, Resselaer, N.Y.); polyethylenimine polymers such as CORCAT™ P-600 (EIT Company, Lake Wylie, S.C.); polyoxyalkyleneamines such as JEFFAMINE.™ D-230, D-400, D-2000, HK-511 (XTJ-511), XTJ-510 (D-4000), XTJ-500 (ED-600), XTJ-502 (ED-2003), T-403, XTJ-509 (T-3000), and T-5000 (Huntsman Corporation, Houston, Tex.); and polyamide resins such as the VERSAMID series of resins that are formed by reacting a dimerized unsaturated fatty acid with alkylene diamines (Cognis Corporation, Cincinnati, Ohio).

The ligand functional polymer may be prepared by condensation of the polyamine polymer with a guanylating agent. Known guanylating agents include: cyanamide; O-alkylisourea salts such as O-methylisourea sulfate, O-methylisourea hydrogen sulfate, O-methylisourea acetate, O-ethylisourea hydrogen sulfate, and O-ethylisourea hydrochloride; chloroformamidine hydrochloride; 1-amidino-1,2, 4-triazole hydrochloride; 3,5-dimethylpyrazole-1-carboxamidine nitrate; pyrazole-1-carboxamidine hydrochloride; N-amidinopyrazole-1-carboxamidine hydrochloride; and carbodiimides, such as dicyclohexylcarbodiimide, N-ethyl-N'-(3-dimethylaminopropyl)carbodiimide, and diisopropylcarbodiimide. The polyamine polymer may also be acylated with guanidino-functional carboxylic acids such as guanidinoacetic acid and 4-guanidinobutyric acid in the presence of activating agents such as EDC (N-[3-(dimethylamino) propyl]-3-ethylcarbodiimide hydrochloride), or EEDQ (2-ethoxy-1-ethoxycarbonyl-1,2-dihydroquinoline). Additionally, the ligand functional polymer may be prepared by alkylation with chloroacetone guanyl hydrazone, as described in U.S. Pat. No. 5,712,027.

Reagents for the preparation of biguanide-functional polymers include sodium dicyanamide, dicyanodiamide and substituted cyanoguanidines such as $N^3$-p-chlorophenyl-$N^1$-cyanoguanidine, $N^3$-phenyl-$N^1$-cyanoguanidine, $N^3$-alpha-naphthyl-$N^1$-cyanoguanidine, $N^3$-methyl-$N^1$-cyanoguanidine, $N^3,N^3$-dimethyl-$N^1$-cyanoguanidine, $N^3$-(2-hydroxyethyl)-$N^1$-cyanoguanidine, and $N^3$-butyl-$N^1$-cyanoguanidine. Alkylene- and arylenebiscyanoguanidines may be utilized to prepare biguanide functional polymers by chain extension reactions. The preparation of cyanoguanidines and biscyanoguanidines is described in detail in Rose, F. L. and Swain, G. J. Chem Soc., 1956, pp. 4422-4425. Other useful guanylating reagents are described by Alan R. Katritzky et al., *Comprehensive Organic Functional Group Transformation*, Vol. 6, p. 640. Generally, such guanylation reagents are used in amounts sufficient to functionalize 0.5 to 100 mole percent, preferably 2.5 to 50 mole percent, of the available amino groups of the aminopolymer.

The resulting polymer will have pendent or catenary guanidinyl groups of the formula:

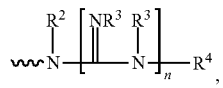

wherein
$R^2$ is a H, $C_1$-$C_{12}$ alkyl, $C_5$-$C_{12}$ (hetero)aryl, or a residue of the polymer chain;
each $R^3$ is independently H, $C_1$-$C_{12}$ alkyl, or $C_5$-$C_{12}$ (hetero)aryl,
each $R^4$ is H, $C_1$-$C_{12}$ alkyl or alkylene, $C_5$-$C_{12}$ (hetero)aryl or (hetero)arylene, cyano,
or —C(=NH)—N($R^2$)-Polymer, and
n is 1 or 2.

In some embodiments, it may be advantageous to functionalize the amine containing polymer with other ligands in addition to the guanidinyl ligand. For example, it may be useful to include a hydrophobic ligand, an ionic ligand, or a hydrogen bonding ligand. This can be particularly advantageous for the capture of certain biological species, especially under conditions of high ionic strength.

The additional ligands are readily incorporated into the ligand functional polymers by alkylation or acylation procedures well known in the art, such as by using halide, sulfonate, or sulfate displacement reactions, or by using epoxide ring opening reactions. Useful alkylating agents for these reactions include, for example, dimethylsulfate, butyl bromide, butyl chloride, benzyl bromide, dodecyl bromide, 2-chloroethanol, bromoacetic acid, 2-chloroethyltrimethylammonium chloride, styrene oxide, glycidyl hexadecyl ether, glycidyltrimethylammonium chloride, and glycidyl phenyl ether. Useful acylating agents include, for example, acid chlorides and anhydrides such as benzoyl chloride, acetic anhydride, succinic anhydride, and decanoyl chloride, and isocyanates such as trimethylsilylisocyanate, phenyl isocyanate, butyl isocyanate, and butyl isothiocyanate. In such embodiments 0.1 to 20 mole percent, preferably 2 to 10 mole percent, of the available amino groups of the aminopolymer may be alkylated and/or acylated.

The disclosure further provides a functionalized substrate comprising a base substrate and an ungrafted coating of the ligand functionalized polymer thereon. Preferably the base substrate is a porous base substrate having interstitial and outer surfaces.

The base substrate may be formed from any suitable metallic, thermoplastic, or thermoset material. The material may be an organic or inorganic polymeric material. Suitable organic polymeric materials include, but are not limited to, poly(meth)acrylates, poly(meth)acrylamides, polyolefins, poly(isoprenes), poly(butadienes), fluorinated polymers, chlorinated polymers, polyamides, polyimides, polyethers, poly(ether sulfones), poly(sulfones), poly(vinyl acetates), copolymers of vinyl acetate, such as poly(ethylene)-co-poly (vinyl alcohol), poly(phosphazenes), poly(vinyl esters), poly (vinyl ethers), poly(vinyl alcohols), and poly(carbonates). Suitable inorganic polymeric materials include, but are not limited to, quartz, silica, glass, diatomaceous earth, and ceramic materials.

Suitable polyolefins include, but are not limited to, poly (ethylene), poly(propylene), poly(1-butene), copolymers of ethylene and propylene, alpha olefin copolymers (such as copolymers of ethylene or propylene with 1-butene, 1-hexene, 1-octene, and 1-decene), poly(ethylene-co-1-butene) and poly(ethylene-co-1-butene-co-1-hexene).

Suitable fluorinated polymers include, but are not limited to, poly(vinyl fluoride), poly(vinylidene fluoride), copolymers of vinylidene fluoride (such as poly(vinylidene fluoride-co-hexafluoropropylene), and copolymers of chlorotrifluoroethylene (such as poly(ethylene-co-chlorotrifluoroethylene).

Suitable polyamides include, but are not limited to, poly (iminoadipoyliminohexamethylene), poly(iminoadipoyliminodecamethylene), and polycaprolactam. Suitable polyimides include, but are not limited to, poly(pyromellitimide).

Suitable poly(ether sulfones) include, but are not limited to, poly(diphenylether sulfone) and poly(diphenylsulfone-co-diphenylene oxide sulfone).

Suitable copolymers of vinyl acetate include, but are not limited to, poly(ethylene-co-vinyl acetate) and such copolymers in which at least some of the acetate groups have been hydrolyzed to afford various poly(vinyl alcohols).

The base substrate may be in any form such as particles, fibers, films or sheets. Suitable particles include, but are not limited to, magnetic particles, organic particles, inorganic particles, and porous and nonporous particles. Preferably the base substrate is porous. Suitable porous base substrates include, but are not limited to, porous particles, porous membranes, porous nonwoven webs, and porous fibers.

In some embodiments, the porous base substrate is formed from propylene homo- or copolymers, most preferably propylene homopolymers. Polypropylene polymers are often a material of choice for porous articles, such as nonwovens and microporous films, due to properties such as non-toxicity, inertness, low cost, and the ease with which it can be extruded, molded, and formed into articles.

In many embodiments, the porous base substrate has an average pore size that is typically greater than about 0.2 micrometers in order to minimize size exclusion separations, minimize diffusion constraints and maximize surface area and separation based on binding of a target molecule. Generally, the pore size is in the range of 0.1 to 10 micrometers, preferably 0.5 to 3 micrometers and most preferably 0.8 to 2 micrometers when used for binding of viruses. The efficiency of binding other target molecules may confer different optimal ranges.

Suitable porous base substrates include, but are not limited to, porous and microporous membranes, nonwoven webs, and fibers. In some embodiments, the porous base substrate is a microporous membrane such as a thermally-induced phase separation (TIPS) membrane. TIPS membranes are often prepared by forming a homogenous solution of a thermoplastic material and a second material above the melting point of the thermoplastic material. Upon cooling, the thermoplastic material crystallizes and phase separates from the second material. The crystallized thermoplastic material is often stretched. The second material is optionally removed either before or after stretching. Microporous membrane are further disclosed in U.S. Pat. No. 4,539,256 (Shipman), U.S. Pat. No. 4,726,989 (Mrozinski), U.S. Pat. No. 4,867,881 (Kinzer), U.S. Pat. No. 5,120,594 (Mrozinski), U.S. Pat. No. 5,260,360 (Mrozinski et al.), and U.S. Pat. No. 5,962,544 (Waller), all of which are assigned to 3M Company (St. Paul, Minn.). Further, the microporous film can be prepared from ethylene-vinyl alcohol copolymers as described in U.S. Pat. No. 5,962,544 (Waller).

Some exemplary TIPS membranes comprise poly(vinylidene fluoride) (PVDF), polyolefins such as polyethylene homo- or copolymers or polypropylene homo- or copolymers, vinyl-containing polymers or copolymers such as ethylene-vinyl alcohol copolymers and butadiene-containing polymers or copolymers, and acrylate-containing polymers or copolymers. For some applications, a TIPS membrane comprising PVDF is particularly desirable. TIPS membranes comprising PVDF are further described in U.S. Pat. No. 7,338,692 (Smith et al.).

In another exemplary embodiment the porous bases substrate comprises a nylon microporous film or sheet, such as those described in U.S. Pat. No. 6,056,529 (Meyering et al.), U.S. Pat. No. 6,267,916 (Meyering et al.), U.S. Pat. No. 6,413,070 (Meyering et al.), U.S. Pat. No. 6,776,940 (Meyering et al.), U.S. Pat. No. 3,876,738 (Marinacchio et al.), U.S. Pat. Nos. 3,928,517, 4,707,265 (Knight et al.), and U.S. Pat. No. 5,458,782 (Hou et al.).

In other embodiments, the porous base substrate is a nonwoven web which may include nonwoven webs manufactured by any of the commonly known processes for producing nonwoven webs. As used herein, the term "nonwoven web" refers to a fabric that has a structure of individual fibers or filaments which are randomly and/or unidirectionally interlaid in a mat-like fashion.

For example, the fibrous nonwoven web can be made by wet laid, carded, air laid, spunlaced, spunbonding or meltblowing techniques or combinations thereof. Spunbonded fibers are typically small diameter fibers that are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to from a web of randomly disbursed meltblown fibers. Any of the nonwoven webs may be made from a single type of fiber or two or more fibers that differ in the type of thermoplastic polymer and/or thickness.

Further details on the manufacturing method of nonwoven webs of this invention may be found in Wente, Superfine Thermoplastic Fibers, 48 INDUS. ENG. CHEM. 1342(1956), or in Wente et al., Manufacture Of Superfine Organic Fibers, (Naval Research Laboratories Report No. 4364, 1954).

In one embodiment the base substrate may have a coating of the ligand functional (co)polymer on a surface thereon. Useful coating techniques include applying a solution or dispersion of the (co)polymer, optionally including a crosslinker, onto the base substrate. Polymer application is generally followed by evaporating the solvent to form the polymer coating. Coating methods include the techniques commonly known as dip, spray, knife, bar, slot, slide, die, roll, or gravure coating. Coating quality generally depends on mixture uniformity, the quality of the deposited liquid layer, and the process used to dry or cure the liquid layer.

In some embodiments, the polyamine polymer is first coated on the base substrate and subsequently reacted with a guanylating agent, such as pyrazole carboxamidine hydrochloride.

In other embodiments, the ligand functional (co)polymer itself is coated on the base substrate. Useful crosslinkers in these instances include amine reactive compounds such as bis- and polyaldehydes such as glutaraldehyde, bis- and polyepoxides such as butanedioldiglycidylether and ethyleneglycoldiglycidylether, polycarboxylic acids and their derivatives (e.g., acid chlorides), polyisocyanates, formaldehyde-based crosslinkers such as hydroxymethyl and alkoxymethyl functional crosslinkers, such as those derived from urea or melamine, and amine-reactive silanes, such as 3-glycidoxypropyltrimethoxysilane, 3-glycidoxypropyltriethoxysilane, 5,6-epoxyhexyltriethoxysilane, (p-chloromethyl)phenyltrimethoxysilane, chloromethyltriethoxysilane, 3-isocyanatopropyltriethoxysilane, and 3-thiocyanatopropyltriethoxysilane.

In other embodiments, the ligand functional copolymer is coated on the base substrate by polyelectrolyte layer-by-layer coating techniques, such as those described in EP 472,990.

In some embodiments, the base substrate has amine-reactive functional groups, such as halide, epoxy, ester, isocyanate groups, on the surface thereof. These surface functional groups may react with extant amine functional groups on the ligand functional aminopolymer. In another embodiment, the surface of the base substrate may be provided with amine-reactive functional groups that can react with the amine groups of the ligand functionalized polymer.

The amine-reactive functional groups may be provided by any of the techniques known to one in the art. In one embodiment the base substrate may have a coating of a (co)polymer comprising amine-reactive functional groups on a surface thereon. Especially useful (co)polymers in this regard are azlactone functional (co)polymers such as those described in U.S. Pat. No. 7,101,621. Useful coating techniques include applying a solution or dispersion of the (co)polymer, optionally including a crosslinker, onto the base substrate. Polymer application is generally followed by evaporating the solvent to form the polymer coating. Coating methods include the techniques commonly known as dip, spray, knife, bar, slot, slide, die, roll, or gravure coating. Coating quality generally depends on mixture uniformity, the quality of the deposited liquid layer, and the process used to dry or cure the liquid layer.

In some embodiments the polymer comprising amine-reactive groups may be grafted to the surface of a substrate by ionizing radiation-initiated graft polymerization of a monomer having a free-radically polymerizable group and a second functional group reactive with the ligand functional polymer, as described in Assignee's copending application US 2010/0075560, incorporated herein by reference. Such monomers may include azlactone-functional monomers, isocyanatoethyl (meth)acrylate or glycidyl (meth)acrylate. Alternatively, a carbonyl functional monomer may be grafted to the surface of a substrate by ionizing radiation-initiated graft polymerization, followed by functionalization by reaction with the ligand functional polymer of Formula I, as described in Assignee's U.S. Pat. No. 8,377,672, incorporated herein by reference.

The method of grafting (or coating) a ligand functionalized polymer to the surface of the substrate alters the original nature of the base substrate, as the substrate bears a grafted or ungrafted coating of the ligand functional polymer. The present invention enables the formation of ligand functionalized polymer substrates having many of the advantages of a base substrate (e.g., mechanical and thermal stability, porosity), but with enhanced affinity for biological species such as viruses, resulting from the monomers and steps used to form a given functionalized substrate.

The porous substrates having a coating of ligand-functionalized polymer are particularly suited as filter media, for the selective binding and removal of target biological species including proteins, cells, cell debris, microbes, nucleic acids, and/or viruses from biological samples. The present disclosure further provides a method for the removal of target biological species from a biological sample by contacting the sample with the ligand polymer functionalized substrate as described herein. As used herein "target biological species" may include a contaminant or a species of interest.

The ligand functionalized (co)polymer (either the polymer per se, or a substrate having a coating thereof) is useful for the purification of biological or other fluid samples comprising biologically derived species (biological species). Biological species include, but are not limited to, cells, cell debris, proteins, nucleic acids, endotoxins, and viruses. Cells and cell debris include those derived from archaea, bacteria, and eucaryotes. Bacteria include, but are not limited to, Gram-negatives such as *Pseudomonas* species, *Escherichia coli, Helicobacter pylori*, and *Serratia marcesens*; Gram-positives such as *Staphylococcus* species, *Enterococcus* species, *Clostridium* species, *Bacillus* species, and *Lactobacillus* species; bacteria that do not stain traditionally by Gram's method such as *Mycobacterium* species, and non-vegetative forms of bacteria such as spores. Eucaryotes include, but are not limited to, animal cells, algae, hybridoma cells, stem cells, cancer cells, plant cells, fungal hyphae, fungal spores, yeast cells, parasites, parasitic oocysts, insect cells, and helminthes. Proteins, include, but are not limited to, natural proteins, recombinant proteins, enzymes, and host cell proteins. Viruses include, but are not limited to, enveloped species such as Herpesviruses, Poxviruses, Adenoviruses, Papovaviruses, Coronaviruses, retroviruses such as HIV, and Plasmaviridae; and non-enveloped species such as Caliciviridae, Corticoviridae, Myoviridae, and Picornaviridae.

In some embodiments, the biological species being removed from the fluid is the object of the purification. For example, a recombinant protein or enzyme may be prepared in cell culture or by fermentation, the (co)polymer can be added to flocculate the protein or enzyme, and the precipitate can be separated as the first step in the purification process for the protein or enzyme. In another example, the (co)polymer or a substrate with a coating thereof, may be used to capture microorganisms from a fluid as the first step in a process of concentrating, enumerating, and/or identifying the microorganisms.

In other embodiments, the biological species being removed from the fluid is a contaminant that must be removed prior to additional processing steps for the fluid. The polymer can be used as a flocculant to facilitate the removal of cells and cell debris from a cell culture or fermentation broth prior to, subsequent to, or in place of a centrifuge or depth filtration operation. For example, the (co)polymer can be used to flocculate cells in a cell culture broth prior to centrifugation, and thereby improve the efficiency with which the centrifugation process separates the cell mass from the liquid centrate. Alternatively, it can be added to the liquid centrate after a centrifugation step to flocculate suspended cell debris and dissolved host cell proteins and nucleic acids, thereby increasing the efficiency of a subsequent depth filtration step. It can be used to flocculate or precipitate suspended bacteria, viruses, or other microorganisms. It can be used to precipitate either desired or contaminating proteins or nucleic acids from solution. Significantly, the ligand functional (co)polymers, or substrates having a coating thereof, are useful under conditions of high salt concentration or high ionic strength, i.e., they are "salt tolerant". The term "salt" is meant to include all low molecular weight ionic species which contribute to the conductivity of the solution. The importance of utility of the ligand functional (co)polymers in the presence of salt is that many process solutions used in biopharmaceutical or enzyme manufacture have conductivities in the range of 15-30 mS/cm (approximately 150-300 mM salt) or more. Salt tolerance can be measured in comparison to that of the conventional quaternary amine or Q ligand (e.g. trimethylammonium ligand), whose primarily electrostatic interactions with many biological species rapidly deteriorates at conductivities three- to six-fold less than the target range. For example, membranes derivatized with the conventional Q ligand exhibit a drop in φX174 viral clearance from a six log-reduction value (LRV) to a one (1) LRV in going from 0 to 50 mM NaCl (ca. 5-6 mS/cm conductivity). Viruses such as φX174 which have pIs close to 7 (are neutral or near-neutral) are extremely difficult to remove from process streams. Similar problems are observed when attempting to remove other biological species from process fluids. For example, when attempting to remove positively charged proteins such as host cell proteins through the use of filtration devices functionalized with conventional Q ligands, the process fluid may have to be diluted two-fold or more in order to reduce the conductivity to an acceptable range. This is expensive and dramatically increases the overall processing time.

When used as a flocculant, the amount of ligand functional polymer that is added relative to the amount of sample can vary over a wide range. Generally, the amount added will produce a final concentration of (co)polymer in the mixture of from about 0.01 micrograms/mL to about 5000 micrograms/mL. The optimal amount of polymer added will depend upon the concentration of the species one desires to flocculate. Typically, the amount of polymer relative to the amount of species being flocculated will be in the range of 0.01% to 100% by weight, preferably 0.05%-30% by weight, more preferably about 0.1%-10% by weight. The optimal amount is readily assessed by challenging the sample with a series of polymer concentrations as is well known in the art. While the above concentration ranges are typical, one skilled in the art will realize that other ranges may work in some instances. Flocculation efficiency also depends upon the physical and chemical characteristics of the species being flocculated. For example, we have found that optimal flocculation of the near neutral virus φX174 from aqueous suspension occurs at a polymer to virus weight ratio of about 800-1000%.

The biological sample is contacted with the ligand functionalized polymer (either the polymer per se, or a substrate having a coating thereof) for a time sufficient to interact and form a complex with the target biological species disposed (dissolved or suspended) in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 50% of its original concentration. It is more preferred that the solution is contacted with the ligand functionalized polymer for a time sufficient to interact and form a complex with the target biological species disposed in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 10% of its original concentration. It is still more preferred that the solution is contacted with the ligand functionalized polymer for a time sufficient to interact and form a complex with the target biological species disposed in the solution when the solution comprises from 0 to about 50 mM salt, preferably when the solution comprises from 0 to about 150 mM salt, more preferably when the solution comprises from 0 to about 300 mM salt or higher, such that the concentration of the target biological species remaining disposed in the solution is less than 1% of its original concentration.

In many embodiments the ligand functionalized polymer, being positively charged in aqueous media, will bind near neutral or negatively charged species to the ligand functional group of Formula II while other species (e.g., positively charged proteins such as monoclonal antibodies) will be excluded or repelled from the ligand functionalized substrate. In addition, as previously described, the substrate may be directly or indirectly grafted with one or more ionic monomers. In particular, the ligand functionalized polymer may comprise grafted ionic groups that are positively charged at the selected pH of the biological sample solution to enhance electrostatic charge repulsion of proteins, such as monoclonal antibodies, many of which are charged positive at neutral pH, and ligand functional groups of Formula II to provide salt tolerance.

In some embodiments the ligand functionalized polymer and coated substrate containing the bound biological species are disposable. In such embodiments, the binding of the biological species to the ligand functionalized polymer is preferably essentially irreversible because there is no need to recover the bound biological species. Nonetheless, if desired, one can reverse the binding of biological species by increasing the ionic strength or changing the pH of an eluting solution.

The substrate, having a grafted or ungrafted coating of the ligand functionalized polymer may be any previously described, but is preferably a microporous membrane. The membrane pore size desired is from 0.1 to 10 μm, preferably 0.5 to 3 micrometers and most preferably 0.8 to 2 micrometers. A membrane with a high surface area for the internal pore structure is desired, which typically corresponds to fine pore sizes. However, if the pore size is too small, then the membrane tends to plug with fine particulates present in the sample solution.

If desired, efficiency of binding and capture may be improved by using a plurality of stacked, ligand functionalized polymer coated porous membranes as a filter element. Thus the present disclosure provides a filter element comprising one or more layers of the porous, ligand functionalized polymer coated substrate. The individual layers may be the same or different, and may have layers of different porosity, and degree of grafting by the aforementioned grafting monomers. The filter element may further comprise an upstream prefilter layer and downstream support layer. The individual filter elements may be planar or pleated as desired.

Examples of suitable prefilter and support layer materials include any suitable porous membranes of polypropylene, polyester, polyamide, resin-bonded or binder-free fibers (e.g., glass fibers), and other synthetics (woven and nonwoven fleece structures); sintered materials such as polyolefins, metals, and ceramics; yarns; special filter papers (e.g., mixtures of fibers, cellulose, polyolefins, and binders); polymer membranes; and others.

In another embodiment, there is provided a filter cartridge including the above-described filter element. In yet another embodiment, there is provided a filter assembly comprising the filter elements and a filter housing. In a further embodiment, this invention relates to a method of capture or removal of a target biological species comprising the steps of:

a) providing the filter element comprising one of more layers of the ligand functionalized base substrate of this disclosure, and b) allowing a moving biological solution containing a target biological species to impinge upon the upstream surface of the filter element for a time sufficient to effect binding of a target biological species.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1. Alkylation of Polyethylenimine (PEI)

Dodecyl bromide (2.32 grams) was added to PEI (40 grams of a 10% by weight solution of PEI (MW=10,000, from Polysciences, Inc., Warrington, Pa.) in ethanol in an 8 ounce glass bottle and sealed. The mixture was heated in a water bath at 50° C. for 20 hours, after which time $^1$H-NMR indicated complete conversion to the alkylated product

Example 2. Guanylation of Alkylated Polyetheyleneamine

A portion of the solution of alkylated product (20 grams) of Example 1 was mixed with pyrazole carboxamidine hydrochloride (0.17 gram, from Sigma-Aldrich, Milwaukee, Wis.). The mixture was allowed to react overnight at ambient temperature, after which time $^1$H-NMR indicated conversion of 2.5% of the amine groups to guanidine groups had occurred.

Examples 3-21

Similar procedures were used to produce alkylated and guanylated PEI's as listed in Table 1.

TABLE 1

| | Modified Polyethylenimines | | | |
|---|---|---|---|---|
| Example | PEI MW | Alkylating agent | % Alkylated | % Guanylated |
| 1 | 10,000 | dodecyl bromide | 10 | 0 |
| 2 | 10,000 | dodecyl bromide | 10 | 2.5 |
| 3 | 10,000 | dodecyl bromide | 5 | 0 |
| 4 | 10,000 | dodecyl bromide | 5 | 2.5 |
| 5 | 10,000 | none | 0 | 2.5 |
| 6 | 10,000 | none | 0 | 12.5 |
| 7 | 10,000 | none | 0 | 25 |
| 8 | 10,000 | benzyl bromide | 10 | 0 |
| 9 | 10,000 | dimethylsulfate | 10 | 0 |
| 10 | 10,000 | butyl bromide | 10 | 0 |
| 11 | 70,000 | none | 0 | 10 |
| 12 | 70,000 | none | 0 | 25 |
| 13 | 70,000 | none | 0 | 50 |
| 14 | 70,000 | butyl bromide | 10 | 0 |
| 15 | 70,000 | dodecyl bromide | 10 | 0 |
| 16 | 70,000 | benzyl bromide | 10 | 0 |
| 17 | 70,000 | dimethylsulfate | 10 | 0 |
| 18 | 70,000 | butyl bromide | 10 | 50 |
| 19 | 70,000 | dodecyl bromide | 10 | 50 |
| 20 | 70,000 | benzyl bromide | 10 | 50 |
| 21 | 70,000 | dimethylsulfate | 10 | 50 |

Example 22-32. Modified Poly(Allylamine)s

Using procedures similar to those described in Example 1, poly(allylamine) (MW 60,000, Polysciences) was reacted with a variety of alkylating agents and pyrazole carboxamidine hydrochloride to provide a series of alkylated, guanylated, or alkylated and guanylated polymers (Table 2).

TABLE 2

| | Modified Poly(allylamines) | | |
|---|---|---|---|
| Example | Alkylating agent | % Alkylated | % Guanylated |
| 22 | dodecyl bromide | 10 | 0 |
| 23 | butyl bromide | 10 | 0 |
| 24 | benzyl bromide | 10 | 0 |
| 25 | dimethylsulfate | 10 | 0 |
| 26 | none | 0 | 10 |
| 27 | none | 0 | 25 |
| 28 | none | 0 | 50 |
| 29 | dodecyl bromide | 10 | 50 |
| 30 | butyl bromide | 10 | 50 |
| 31 | benzyl bromide | 10 | 50 |
| 32 | dimethylsulfate | 10 | 50 |

Comparative Example 1. Poly(Methacrylamidopropyltrimethylammonium Chloride) (pMAPTAC)

MAPTAC (160 grams of a 50% by weight solution in water, from Aldrich, Milwaukee, Wis.), ethanol (40 grams) and sodium persulfate (0.4 gram) were charged to a 16 ounce glass bottle. The mixture was purged with a slow stream of nitrogen gas for 10 minutes, sealed, and then tumbled in a water bath equilibrated to 55° C. for 24 hours to convert the monomer to polymer. This polymer solution was diluted with deionized water (80 grams) and ethanol (40 grams) and mixed well. A sample for evaluation as a flocculant was prepared by dilution of a portion of this polymer to 1% solids by weight with deionized water, pH 7.

Example 33

A solution of bovine serum albumin (BSA, Sigma-Aldrich) was prepared in 10 mM MOPS, pH 7.5, and determined to have a concentration of BSA of 4.02 mg/mL. A series of BSA solutions were prepared containing various concentrations of sodium chloride according to Table 3.

TABLE 3

| | BSA Solutions | | |
|---|---|---|---|
| [NaCl] (mM, final) | BSA solution (mL) | 5M NaCl (μL) | MOPS buffer (μL) |
| 0 | 10 | 0 | 500 |
| 50 | 10 | 100 | 400 |
| 100 | 10 | 200 | 300 |
| 150 | 10 | 300 | 200 |
| 200 | 10 | 400 | 100 |
| 250 | 10 | 500 | 0 |

Solutions of the polymers from Examples 5, 6, and 7 were diluted with deionized water to 1% solids by weight, pH 7. A 1% solids solution of PEI (10,000 MW) in DI water, pH 7, was also prepared as a control.

A 5 mL polypropylene centrifuge tube was charged with 2.0 mL of BSA solution, followed by 125 μL of diluted polymer solution. The centrifuge tube was sealed and tumbled end over end for 30 minutes, then centrifuged at 2000 rcf for 10 minutes. A BSA standard solution was prepared by mixing 2 mL of original BSA solution with 125 μL of MOPS buffer. A serial 1:1 dilution was performed to provide a total of 7 BSA standards. These seven standards were pipetted (200 μL) in triplicate into wells of a 96-well microtitration plate, along with triplicate samples of the supernates from each polymeric flocculant being evaluated. Three wells containing DI water as a blank were also included. The plate was analyzed using a SpectraMAX 250 Microplate Spectrophotometer System (Molecular Devices Corp, Sunnyvale, Calif.) using a wavelength of 293 nm.

Comparison of the absorptions of the flocculant solutions to those of the standards provided a measure of the flocculation efficiency. Results are recorded as the percentage of starting BSA remaining in solution; thus, the lower the number, the better the flocculant. Results are presented in the following Table 4:

TABLE 4

| Polymer | % BSA Remaining | | | | | |
|---|---|---|---|---|---|---|
| | 0 mM NaCl | 50 mM NaCl | 100 mM NaCl | 150 mM NaCl | 200 mM NaCl | 250 mM NaCl |
| PEI (10,000) | 0.0 | 40.6 | 87.2 | 96.1 | 101.6 | 99.7 |
| Example 5 | 0.9 | 6.2 | 29.3 | 53.9 | 83.4 | 96.8 |
| Example 6 | 0.0 | 5.6 | 28.0 | 51.2 | 79.0 | 93.8 |
| Example 7 | 0.3 | 18.2 | 40.3 | 60.8 | 78.1 | 88.3 |
| Comparative Example 1 | 0.0 | 42.1 | 73.3 | 101.9 | 103.1 | 99.3 |

This example illustrates that incorporation of as little as 2.5% guanidine groups into PEI dramatically improves its ability to precipitate proteins in the presence of sodium chloride.

Example 34

Guanylated PEIs from Examples 11-13 were assayed for BSA precipitation by the procedure described in Example 33, except that 250 μL of 1% solids polymer solution was used instead of 125 μL. Results are shown in Table 4, compared to a control unmodified 70,000 MW PEI.

TABLE 5

| Polymer | % BSA Remaining | | | | |
|---|---|---|---|---|---|
| | 50 mM NaCl | 100 mM NaCl | 150 mM NaCl | 200 mM NaCl | 250 mM NaCl |
| PEI (70,000) | 54.4 | 28.8 | 35.4 | 60.0 | 87.9 |
| Example 11 | 11.1 | 11.5 | 14.4 | 27.6 | 41.1 |
| Example 12 | 17.7 | 7.4 | 9.0 | 13.1 | 95.6 |
| Example 13 | 17.6 | 16.7 | 20.2 | 27.8 | 39.1 |

Example 35

Figure 2:
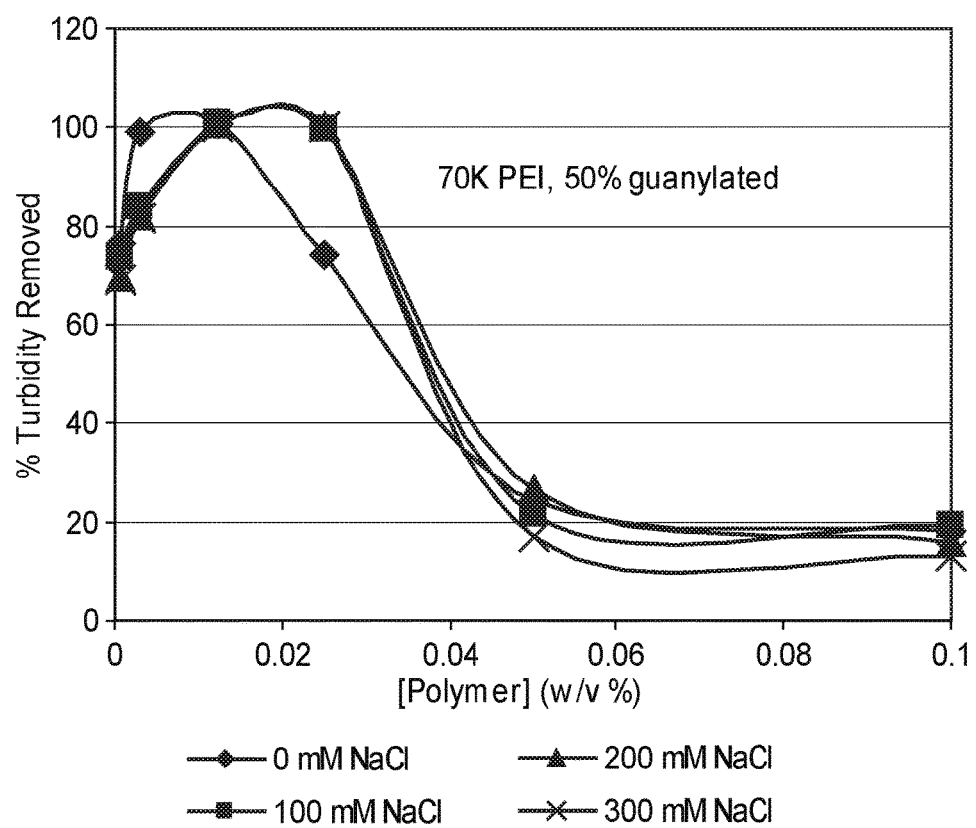
Figure 3:
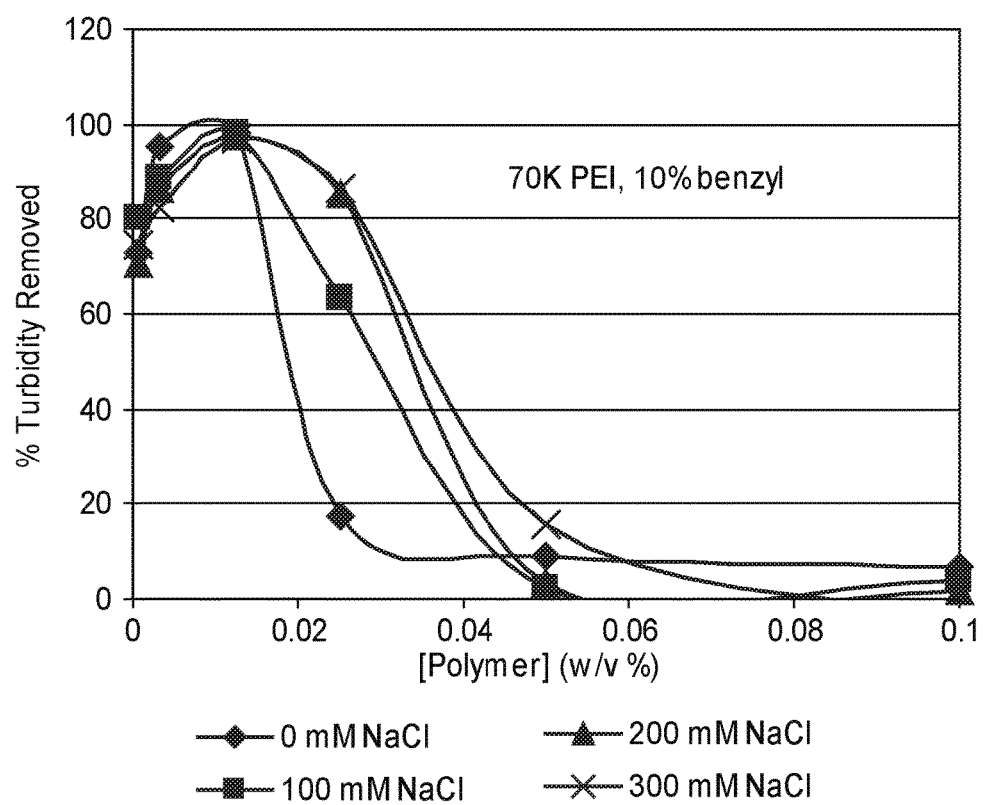
Figure 4:
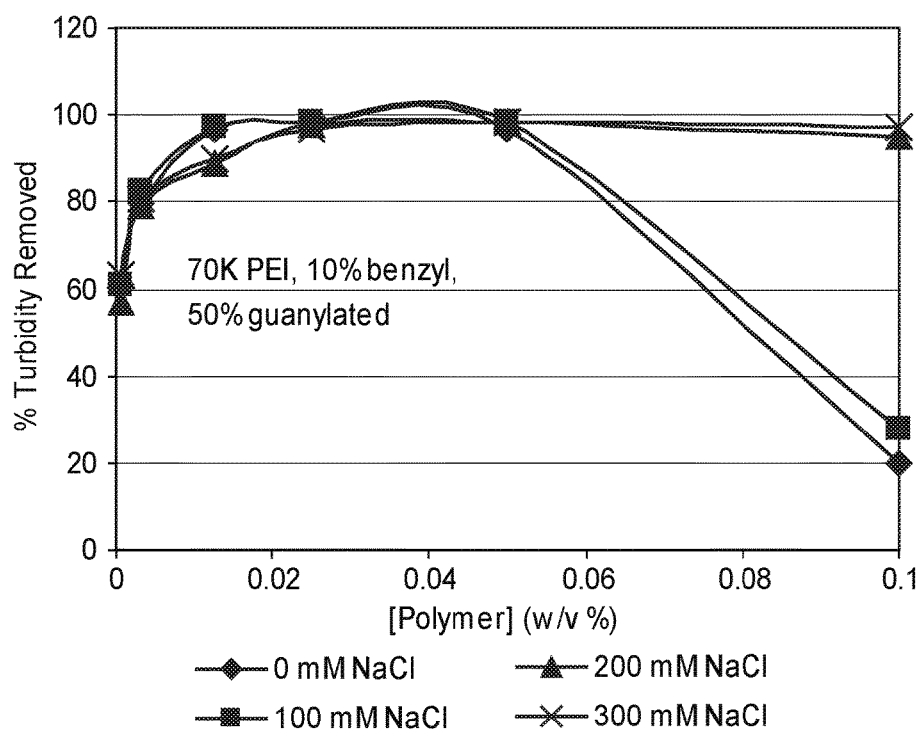

A *Geobacillus stearothermophilus* cell culture broth was provided by 3M consisting of approximately 1.4% by weight cell debris and spores. Test samples of broth were prepared containing 0, 100, 200, and 300 mM NaCl by a procedure similar to that described in Example 33. Solutions of polymers were prepared at 0.5% solids in DI water from 70,000 MW PEI and from the modified polymers of Examples 13, 16, and 20. A dilution series of each of these polymers was prepared (1:4, 1:4, 1:2, 1:2, 1:2) to provide a total of 6 polymer concentrations. Then 2 mL of broth sample was mixed with 0.5 mL of polymer solution, and the mixture was tumbled for 30 minutes, then centrifuged at 200 rcf for 5 minutes. Standards were prepared by mixing 2 mL of broth with 0.5 mL of DI water, carrying the mixture through the same mixing/centrifugation procedure, then preparing a 2-fold serial dilution (6 samples) from the supernate. Supernates from the test solutions and from the standards were pipetted into a 96-well microtitration plate and assayed by absorbance measurement at 650 nm. Comparison of the absorptions of the flocculant solutions to those of the standards provided a measure of the flocculation efficiencies. Results are presented in the FIGS. 1-4 which show the removal of turbidity at different salt concentrations and different polymer concentrations for an unmodified PEI polymer (FIG. 1), a guanylated PEI polymer (FIG. 2), an alkylated PEI polymer (FIG. 3), and a polymer that has been alkylated and guanylated (FIG. 4).

Similar results were observed for Examples 14, 15, 17, 18, 19, and 21; that is, alkylation of the PEI resulted in broadening the concentration range in which the flocculant was effective in higher salt concentrations, while alkylation plus guanylation were synergistic in this regard.

By making minor modifications to the assay procedure, similar flocculation studies on a *Bacillus atrophaeus* cell culture broth (2.2% by weight vegetative cells, cell debris, and spores), and a *Clostridum sporogenes* purified spore suspension (0.013% solids) were conducted and similar results were observed.

Example 36. Virus Flocculation

Aqueous suspensions of φX174 bacteriophage (ca. $10^9$ pfu/mL) were prepared in 10 mM TRIS((hydroxymethyl)aminomethane) pH 8.0 containing 0, 50 mM, and 150 mM NaCl. Aqueous solutions of flocculator polymers were prepared in DI water, pH 7, at 0.001% polymer by weight. 16 μL of polymer solution were added to a 2 mL sample of bacteriophage suspension in a centrifuge tube. The tube was sealed, vortexed, and rotated end-over-end for 2 hours. The tubes were then centrifuged at 3000 rcf for 10 minutes, and the resultant suspensions were filtered through a 0.45 micron sterile syringe filter (GHP Acrodisc, Pall Life Sciences). A 10-fold dilution series was prepared.

One mL of each dilution was mixed with 1 mL *E. coli* culture (grown to an optical density of 0.3-0.6 when measured at 550 nm). After waiting 5 minutes, a sterile pipet was used to mix 4.5 mL TSA Top agar with the dilution/*E. coli* mixture and plated on TSB plates. After the top agar had solidified, the plates were inverted and placed in a 37° C. incubator overnight. Plates were then removed from the incubator and φX174 plaques were counted and recorded. A dilution series of the original virus suspension was also evaluated in a similar manner. Comparison of the results allowed estimation of the LRV (log reduction in viral load) as a result of the flocculant treatment. Results for several polymers are listed in Table 6:

TABLE 6

| | Virus LRV | | |
| --- | --- | --- | --- |
| | PhiX174 LRV | | |
| Polymer | 0 mM NaCl | 50 mM NaCl | 150 mM NaCl |
| Comparative Example 1 | 6.3 | 0.1 | 0.5 |
| Example 27 | 5.8 | 3.5 | 2.9 |
| Example 11 | 8.5 | 3.4 | 2.0 |
| Example 12 | 8.5 | 3.8 | 1.9 |
| Example 13 | >8 | 6.3 | 2.9 |

Example 37

Five coating baths were prepared:
Coating Bath #1: 0.5% wt/wt poly(2-acrylamido-2-methyl-1-propanesulfonic acid, sodium salt) in deionized water;
Coating Bath #2: 1% wt/wt polyethylenimine (10,000 Mn) in deionized water;
Coating Bath #'s 3-5: 1% wt/wt polymer of Examples 5, 6, or 7, respectively, in deionized water.
Aminosilane coated glass microscope slides (obtained from Newcomer Supply, Middleton, Wis.) were dip coated, in sequence, with coating solution #1, rinsed with deionized water, and dried at room temperature. Slides were then dip coated in coating solution #2 (control), #3, #4, or #5, rinsed with deionized water, and dried at room temperature. The coated slides could then be used to capture bacteria or spores from aqueous media for enumeration or for identification. A control aminosilane slide coated with only coating solution #1 was found to bind almost no bacteria or spores.

Slides coated with PEI and the modified PEIs of Examples 5-7 were evaluated for their ability to capture *Clostridium sporogenes* spores by the following procedure:

Prepare a suspension of pure *C. sporogenes* spores at approximately 1×10⁸ CFU/mL in 40% ethyl alcohol, 60% water. Centrifuge between 0.5 and 1.0 mL of the spore suspension (volume will depend on number of materials tested), discard the supernatant and re-suspend 1:1 in 70% ethyl alcohol in water. Next place three replicates of coated microscope slides into a square Petri dish and apply 10 μl of the spore suspension 0.5 cm from the bottom in the center of the slide. Leave for 1 minute then rinse each slide under a steady stream of ultrapure water from a Milli-Q system at a flow rate of approximately 1.2 liters per minute for 10 seconds. Now dry the slide using a gentle flow of nitrogen gas. Using a light microscope, place the spore-exposed portion of the slide under the 10× objective and randomly capture images of three separate areas within the exposed region. Count the number of spores in each image; this can be done by hand or alternately using image processing software such as AxioVision (Zeiss). Calculate the average per slide based on the counts from the three images on the same slide. Finally, calculate the average and standard deviation per material from the three replicates.

The results are displayed in Table 7:

TABLE 7

| | Coating: | | | |
|---|---|---|---|---|
| | PEI | Example 5 | Example 6 | Example 7 |
| # of Spores Captured: | 664 | 1392 | 1347 | 1050 |

Example 38. p-Chlorophenylbiguanide Derivative of PEI

A solution of 2.00 grams of PEI (MW=10,000, from Polysciences, Inc., Warrington, Pa.) in 10 mL of ethoxyethanol was treated with 2.93 mL of 1.0N aqueous hydrochloric acid solution. $N^3$-p-chlorophenyl-$N^1$cyanoguanidine (570 mg, 2.94 mmol) was added and the reaction mixture was heated to 140° C. overnight. Thin layer chromatography indicated that all of the $N^3$-p-chlorophenyl-$N^1$cyanoguanidine had been consumed. The reaction mixture was concentrated under reduced pressure to give an orange syrup. $^1$H-NMR indicated conversion to the p-chlorophenylbiguanide product. The resulting syrup was dissolved in water to give a 20% by wt solution based on the PEI initial mass.

Evaluation of this polymer by the BSA precipitation test described in Example 33, using 250 μL flocculant solution, showed good BSA removal at all salt concentrations, up to 250 mM, tested.

Examples 39-44. Carbodiimide Modifications of PEI

A solution of 1.05 grams of PEI (MW=10,000, from Polysciences, Inc., Warrington, Pa.) in 10 mL of tert-butyl alcohol was placed in a vial and treated with enough dicyclohexycarbodiimide (314 mg, 1.52 mmol) to react with 6.3% of the amine groups. The vial was sealed and the mixture was heated at 100° C. overnight. The reaction mixture was concentrated under reduced pressure to give a colorless syrup. $^1$H-NMR indicated conversion to the dicyclohexyl guanide product (Example 39). Likewise, PEI samples functionalized with 12.5% and 25% dicyclohexyl guanides were also prepared (Examples 40 and 41, respectively). The resulting syrups with 6.3 and 12.5% dicyclohexyl guanides were dissolved in dilute hydrochloric acid to give a 10% by wt solution based on the initial PEI mass. The product with 25% dicyclohexyl guanides was dissolved in 1:1 ethanol/dilute hydrochloric acid to give a 5% by wt solution based on the initial PEI mass.

A solution of 0.99 grams of PEI (MW=10,000, from Polysciences, Inc., Warrington, Pa.) in 10 mL of tert-butyl alcohol was placed in a vial and treated with enough N[3-(dimethylamino)propyl]-3-ethylcarbodiimide hydrochloride (280 mg, 1.46 mmol) to react with 6.3% of the amine groups. The vial was sealed and the mixture was heated at 100° C. overnight. The reaction mixture was concentrated under reduced pressure to give a colorless syrup. $^1$H-NMR indicated conversion to the desired guanide product (Example 42). Likewise, PEI samples functionalized with 12.5% and 25% N-[3-(dimethylamino)propyl]-3-ethylcarbodiimide were also prepared (Examples 43 and 44, respectively). The resulting syrups were dissolved water to give a 10% by wt solution based on the initial PEI mass.

Polymers of Examples 39 and 41 were diluted to 1% solids and evaluated for BSA precipitation using 250 μL flocculant solution. Results are displayed in Table 8, along with those for unmodified PEI:

TABLE 8

| | % BSA Remaining | | | | |
|---|---|---|---|---|---|
| Polymer | 50 mM NaCl | 100 mM NaCl | 150 mM NaCl | 200 mM NaCl | 250 mM NaCl |
| PEI (10,000) | 4.0 | 12.5 | 40.0 | 83.7 | 92.8 |
| Example 39 | 3.8 | 10.5 | 27.3 | 63.6 | 80.9 |
| Example 41 | 4.6 | 8.0 | 17.6 | 39.9 | 47.0 |

Example 45

The polymer of Example 11 was diluted to 0.5% solids with isopropanol. Four portions of this solution (50 grams each) were formulated with enough butanediol diglycidyl ether (BUDGE) to react with 2.5%, 5%, 10%, and 20%, respectively, of the amine groups of the polymer. Samples (ca. 10 cm×10 cm) of a nylon 66 membrane (single reinforced layer nylon three zone membrane, nominal pore size 1.8 µm, from 3M Purification Inc, Meridan, Conn.), were dip coated with the polymer solution, excess coating solution was removed using a #14 wire-wound coating rod, then allowed to dry for 15 minutes. In some instances, a second coating layer was applied. The coated membranes were then placed in 500 mL polyethylene bottles filled with deionized water and allowed to mix overnight to extract any non-crosslinked coating. Disks (24 mm diameter) were punched out of the membranes and placed in 5 mL centrifuge tubes. Bovine serum albumin solution (BSA, Sigma Aldrich) was prepared to a concentration of 1.1 mg/ml in 25 mM TRIS buffer, pH 8.0 (tris(hydroxymethyl)aminomethane, Sigma). 4.5 ml of the BSA solution was pipetted into each centrifuge tube, the tubes were capped, and the tubes were tumbled overnight. The supernatant solutions were analyzed by a UV-VIS spectrometer at 279 nm with background correction applied at 325 nm. Static binding capacities for the samples are listed in Table along with that for an uncoated membrane.

TABLE 9

| % Crosslinker (BUDGE) | # of Coating Layers | Static BSA Capacity (mg/mL) |
|---|---|---|
| 2.5 | 1 | 15 |
| 2.5 | 2 | 20 |
| 5 | 1 | 17 |
| 5 | 2 | 26 |
| 10 | 1 | 19 |
| 10 | 2 | 35 |
| 20 | 1 | 27 |
| 20 | 2 | 46 |
| 0 | 0 | 1 |

Examples 46-48. Cyanoguanidine-Derivatized PEI

A solution of 2.01 grams of PEI (MW=10,000, from Polysciences, Inc., Warrington, Pa.) in 11.7 mL of 0.1N aqueous hydrochloric acid was placed in a pressure flask and treated with enough sodium dicyanamide (104 mg, 1.17 mmol) to react with 2.5% of the amine groups. The flask was sealed and the mixture was heated at 120° C. for 5 hours. $^1$H-NMR indicated conversion to the cyanoguanidine product (Example 46).

Likewise, a 1.96 g solution of PEI dissolved in 9 mL of water was treated with 2.9 mL of 1.0N hydrochloric acid and sodium dicyanamide (255 mg, 2.86 mmol) to give a product where 6.3% of the amines were converted to cyanoguanides and a 1.99 g solution of PEI dissolved in 6 mL of water was treated with 5.8 mL of 1.0N hydrochloric acid and sodium dicyanamide (520 mg, 5.84 mmol) to give a product where 12.5% of the amines were converted to cyanoguanides (Examples 47 and 48, respectively).

Examples 49-51. Urea Modification of PEI

A solution of 3.00 grams of PEI (MW=10,000, from Polysciences, Inc., Warrington, Pa.) in 15 mL of $CH_2Cl_2$ was treated with enough trimethylsilyl isocyante (235 µL, 1.74 mmol) to react with 2.5% of the amine groups. After stirring for 1 h, the reaction mixture was treated with a few drops of methanol and concentrated under reduced pressure. $^1$H-NMR indicated conversion to the urea product (Example 49). The resulting syrup was dissolved in water to give a 20% by wt solution based on the PEI initial mass. Likewise, PEI functionalized with 6.3% and 12.5% ureas were also prepared (Examples 50 and 51, respectively).

Examples 52-54

The urea modified PEI materials from Examples 49-51, were each reacted with enough pyrazole-1-carboxamidine hydrochloride, by procedures similar to that used in Example 1, to convert 5% of the amine groups to guanidines. $^1$H-NMR indicated conversion to the expected derivatized products (Examples 52-54, respectively).

Example 55. PEI Biguanide

A solution of 92 mg of PEI (MW=10,000, from Polysciences, Inc., Warrington, Pa.) in 0.9 mL of water was placed in a vial and treated with N-amidinopyrazole-carboxamidine hydrochloride (100 mg, 0.53 mmol) to react with 25% of the amine groups. The vial was sealed and the mixture was heated at 100° C. overnight. $^1$H-NMR indicated conversion to the desired guanide product.

Example 56. Poly(polyethylenimine biguanide)

A solution of 1.00 grams of PEI (MW=600, from Polysciences, Inc., Warrington, Pa.) in 10 mL of water was placed in a pressure flask and treated with sodium dicyanamide (139 mg, 1.56 mmol) and 200 µL of acetic acid. The flask was sealed and the mixture was heated at 140° C. overnight. $^1$H-NMR indicated conversion to the polybiguanidine product.

In a similar manner, PEI polymers of different molecular weights can be utilized, and differing ratios of PEI to sodium dicyanamide can be utilized, to prepare a variety of poly(PEI biguanide)s.

Examples 57-59. Modification with Guanidinoacetic Acid

Guanidinoacetic acid (6.0 grams) was dissolved in 1N aqueous hydrochloric acid (51.4 mL). 2-Ethoxy-1-ethoxycarbonyl-1,2-dihydroquinoline (14 grams) was dissolved in an ethanol (25 grams)/methanol (11 grams) mixture. The two solutions were then mixed, and allowed to react for 10 minutes. A portion of this mixture (15.3 grams) was added to a PEI solution (16.67 grams of a 30% solids 70,000 MW PEI solution in water). This mixture was allowed to react for 6 hours to acylate 6.3% of the amine groups of the PEI (Example 57). By similar procedures, modified polymers having 12.5% and 20% of the amine groups acylated were prepared (Examples 58 and 59, respectively).

A portion of the polymer solution of Example 59 was diluted to 1% by weight in deionized water, pH 7, and evaluated in the BSA precipitation test, providing excellent flocculation at all salt concentrations.

Example 60

Using standard microbiological procedures, cultures of the following were prepared:

a) *Escherichia coli* (cells and cell debris)
b) Chinese hamster ovary (CHO) cells
c) Baker's yeast When flocculation experiments were conducted similarly to those described in Example 35 on these mixtures, the ligand functional polymers of the invention consistently displayed good flocculating ability in the presence of sodium chloride concentrations in excess of 50 mM.

The invention claimed is:

1. A method of separating a target biological species from a fluid, wherein the target biological species is neutral or negatively charged, and wherein the fluid is a cell culture or fermentation broth, comprising:
   a. contacting the fluid with a suspension or solution of water-soluble or water-dispersible aminopolymer functionalized with pendent or catenary guanidinyl groups represented by the following general formula:

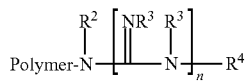

wherein
   $R^2$ is H, $C_1$-$C_{12}$ alkyl, $C_5$-$C_{12}$ (hetero)aryl, or a residue of the polymer chain;
   each $R^3$ is independently H, $C_1$-$C_{12}$ alkyl, or $C_5$-$C_{12}$ (hetero)aryl,
   each $R^4$ is H, $C_1$-$C_{12}$ alkyl or alkylene, $C_5$-$C_{12}$ (hetero)aryl or (hetero)arylene, cyano, or —C(=NH)—N($R^2$)-Polymer,
   n is 1 or 2; and
   "Polymer-N($R^2$)—" is the linkage formed between an amine group of the polyamino polymer and guanylating agent;
   b. forming a complex in the fluid that comprises the aminopolymer functionalized with guanidinyl groups and the target biological species; and
   c. separating the complex from the fluid;
   wherein the target biological species is selected from biomacromolecules and microbiological species.

2. The method according to claim 1, wherein the aminopolymer functionalized with guanidinyl groups is prepared from aminopolymer selected from the group consisting of polyethylenimine, polylysine, polyaminoamides, polyallylamine, polyvinylamine, polydimethylamine-epichlorohydrin-ethylenediamine, polyaminosiloxanes and dendrimers formed form polyamidoamine (PAMAM) and polypropylenimine.

3. The method according to claim 2, wherein the aminopolymer is polyethylenimine or polyallylamine.

4. The method according to claim 1, wherein 0.1 to 20 mole percent of the available amino groups of the aminopolymer functionalized with guanidinyl groups are alkylated and/or acylated.

5. The method according to claim 1, wherein 2 to 10 mole percent of the available amino groups of the aminopolymer functionalized with guanidinyl groups are alkylated and/or acylated.

6. The method according to claim 1, wherein the aminopolymer functionalized with guanidinyl groups is salt tolerant.

7. The method according to claim 6, wherein 0.1 to 20 mole percent of the available amino groups of the aminopolymer functionalized with guanidinyl groups are alkylated and acylated.

8. The method of claim 1, wherein sufficient guanylation agent is used to prepare the aminopolymer functionalized with guanidinyl groups to result in 2.5 to 50 mole percent of the available amino groups of the aminopolymer being functionalized with guanidinyl groups.

9. The method of claim 1, wherein the target biological species is cells or cell debris.

10. The method according to claim 1, wherein after separation step (c), the fluid comprises protein or enzyme.

11. The method according to claim 1, wherein after separation step (c), the fluid comprises antibodies.

12. The method according to claim 1, wherein the salt concentration of the fluid is between 0 and 300 millimolar.

13. The method according to claim 12, wherein the salt concentration of fluid is between 150 to 300 millimolar.

14. The method according to claim 1, wherein the salt concentration of the fluid is at least 150 mM.

15. The method according to claim 12, wherein the target biological species remaining disposed in the fluid after separation step (c) is less than 50% of its concentration in the fluid in step (a).

16. The method according to claim 12, wherein the target biological species remaining disposed in the fluid after separation is less than 10% of its concentration in the fluid in step (a).

17. The method according to claim 12, wherein the target biological species remaining disposed in the fluid after separation is less than 1% of its concentration in the fluid in step (a).

18. The method according to claim 1 wherein the fluid in has a conductivity in the range of 15 to 30 mS/cm.

19. The method according to claim 18, wherein the target biological species remaining disposed in the fluid after separation step (c) is less than 50% of its concentration in the fluid in step (a).

20. The method according to claim 1, wherein the amount of aminopolymer functionalized with guanidinyl groups relative to the amount of target biological species is 0.01% to 100% by weight.

21. The method according to claim 20, wherein the amount of aminopolymer functionalized with guanidinyl groups relative to the amount of target biological species is 0.1%-10% by weight.

22. The method of claim 1 wherein the aminopolymer functionalized with guanidinyl groups is present in amounts of 0.01 to 5000 micrograms/mL of fluid.

23. The method according to claim 1, wherein the complex precipitates from the fluid.

* * * * *